US012700491B1

(12) United States Patent  
Levanon et al.

(10) Patent No.: US 12,700,491 B1  
(45) Date of Patent: Aug. 4, 2026

(54) SYSTEMS AND METHODS FOR ADAPTIVE EXERCISE ROUTINES FOR AN ELECTRONIC EXERCISE MACHINE

(71) Applicant: AMP FIT ISRAEL LTD, Tel Aviv (IL)

(72) Inventors: Amir Levanon, Sunnyvale, CA (US); Tal Soffer, Ramat Gan (IL); Rebecca Shultz, San Carlos, CA (US)

(73) Assignee: AMP FIT ISRAEL LTD, Tel Aviv (IL)

( * ) Notice: Subject to any disclaimer, the term of this patent is extended or adjusted under 35 U.S.C. 154(b) by 24 days.

(21) Appl. No.: 18/541,376

(22) Filed: Dec. 15, 2023

Related U.S. Application Data

(60) Provisional application No. 63/433,463, filed on Dec. 18, 2022, provisional application No. 63/496,605, filed on Apr. 17, 2023.

(51) Int. Cl.  
*G16H 20/30* (2018.01)

(52) U.S. Cl.  
CPC .................................. *G16H 20/30* (2018.01)

(58) Field of Classification Search  
CPC ...................................................... G16H 20/30  
USPC ......................................................... 705/2–3  
See application file for complete search history.

(56) References Cited

U.S. PATENT DOCUMENTS

2019/0005373 A1    1/2019  Nims et al.  
2019/0126099 A1    5/2019  Hoang

2021/0169417 A1*    6/2021  Burton ................. A61B 5/4857  
2022/0047921 A1*    2/2022  Bissonnette ....... A63B 24/0006  
2022/0118304 A1*    4/2022  McNally .............. A63B 21/159  
2023/0089962 A1     3/2023  Shavit

FOREIGN PATENT DOCUMENTS

WO    WO-2021081094 A1 *   4/2021   ........... A61B 5/0022

OTHER PUBLICATIONS

Asadi, 2022, A guide to exercise prescription in adults minimally affected by Multiple Sclerosis (Doctoral dissertation, California State University, Sacramento), https://scholars.csus.edu/view/delivery/01CALS_USL/12245504730001671/13246694650001671 (Year: 2022).*

(Continued)

*Primary Examiner* — Joy Chng  
(74) *Attorney, Agent, or Firm* — Finnegan, Henderson, Farabow, Garrett & Dunner LLP

(57) ABSTRACT

Systems and methods include at least one processor performing adaptive exercise schedule modification operations comprising initially accessing exercise-related data, and based on the exercise-related data, controlling electronic exercise equipment to initiate an exercise session of an initial predetermined duration. The exercise session includes a series of varied electronically controlled exercises selected to further an exercise goal. The operations further include receiving input to modify the initial predetermined duration to an alternative duration, subsequently accessing the exercise-related data, and based on the alternative duration, the exercise-related data, a record of the series, and the exercise goal, adjusting the exercise session by altering a time of the exercise session and in a manner furthering the exercise goal.

22 Claims, 11 Drawing Sheets

(56)         References Cited

OTHER PUBLICATIONS

Bayoumy et al., Smart wearable devices in cardiovascular care: where we are and how to move forward, 2021, Smart Wearable Devices In Cardiovascular Care: Where We Are And How To Move Forward, Nature 18(8), pp. 581-599, https://europepmc.org/ article/ med/33664502 (Year: 2021).*

* cited by examiner

510
Initially access exercise-related data

520
Initiate an exercise session of an initial predetermined duration based on exercise-related data.

530
Receive input to modify the exercise session

540
Subsequently access the exercise-related data.

550
Adjust the exercise session

SYSTEMS AND METHODS FOR ADAPTIVE EXERCISE ROUTINES FOR AN ELECTRONIC EXERCISE MACHINE

CROSS REFERENCE TO RELATED APPLICATIONS

This application claims the benefit of priority of U.S. Provisional Patent Application No. 63/433,463, filed on Dec. 18, 2022; and U.S. Provisional Patent Application No. 63/496,605, filed on Apr. 17, 2023, both of which are incorporated herein by reference in their entirety.

TECHNICAL FIELD

This disclosure relates to systems, methods, and computer readable media associated with adaptive exercise routines for an electronic wall-mounted exercise machines.

BACKGROUND

Resistance training promotes the building and strengthening of muscles and bone tissue, and burns fat. While electronic exercise machines may facilitate resistance training, such machines tend to be large, bulky, and heavy. Wall mounted exercise machines may require a significant amount of wall space, limiting where such machines may be mounted from both physical and esthetic considerations. In addition, wall mounted exercise machines may have numerous controls and adjustment mechanisms that may be cumbersome to use. For example, some exercise machines have mechanical and/or electrical controls that require two-handed adjustments. Some electronic exercise systems may be programmed with predefined routines, that while providing some degree of convenience, may offer only limited adjustment or customization capability to accommodate individual users. Consequently, some electronic exercise systems may be awkward or difficult to use and may discourage users from engaging in exercise routines beneficial to their health. Therefore, there is a need for unconventional innovative streamlined technologies that occupy less space and offer a convenient interface to allow adjusting and customizing exercise routines to suit individual needs.

SUMMARY

Embodiments consistent with the present disclosure provide systems, methods, and devices for adapting exercise routines for electronic exercise machines.

Sometimes during a workout of a predefined length, a user/exerciser may desire to shorten the workout. Rather than simply truncating an in-progress workout, disclosed embodiments may permit the exerciser to modify the workout duration, and in response, use historical data to shorten the workout in a manner that is customized to the user.

Some embodiments involve systems, methods, and non-transitory computer readable medium for performing adaptive exercise routine modification operations. The operations may include obtaining data from an individual, the data relating to physical exercise; based at least in part on the data, defining an initial exercise routine having an exercise routine duration, a set of exercises for the initial exercise routine, and associated achievement goals for the initial exercise routine; receiving a request from the individual to revise the initial exercise routine; and in response to the request, calculating a new exercise routine to comply with the request, wherein the new exercise routine conforms to the achievement goals of the initial exercise routine Some embodiments involve systems and methods and computer readable media for performing adaptive exercise schedule modifications. Related operations may involve accessing exercise-related data, and based on the exercise-related data, controlling electronic exercise equipment to initiate an exercise session of an initial predetermined duration, the exercise session including a series of varied electronically controlled exercises selected to further an exercise goal. A processor may receive input to modify the initial predetermined duration to an alternative duration, subsequently accessing the exercise-related data, and based on the alternative duration, the exercise-related data, the record of the series, and the exercise goal, adjusting the exercise session by altering a time of the exercise session and in a manner furthering the exercise goal.

Consistent with other disclosed embodiments, non-transitory computer-readable storage media may store program instructions, which are executed by at least one processing device and perform any of the methods described herein.

The foregoing general description and the following detailed description are exemplary and explanatory only and are not restrictive of the claims.

DETAILED DESCRIPTION

Figure 1A:
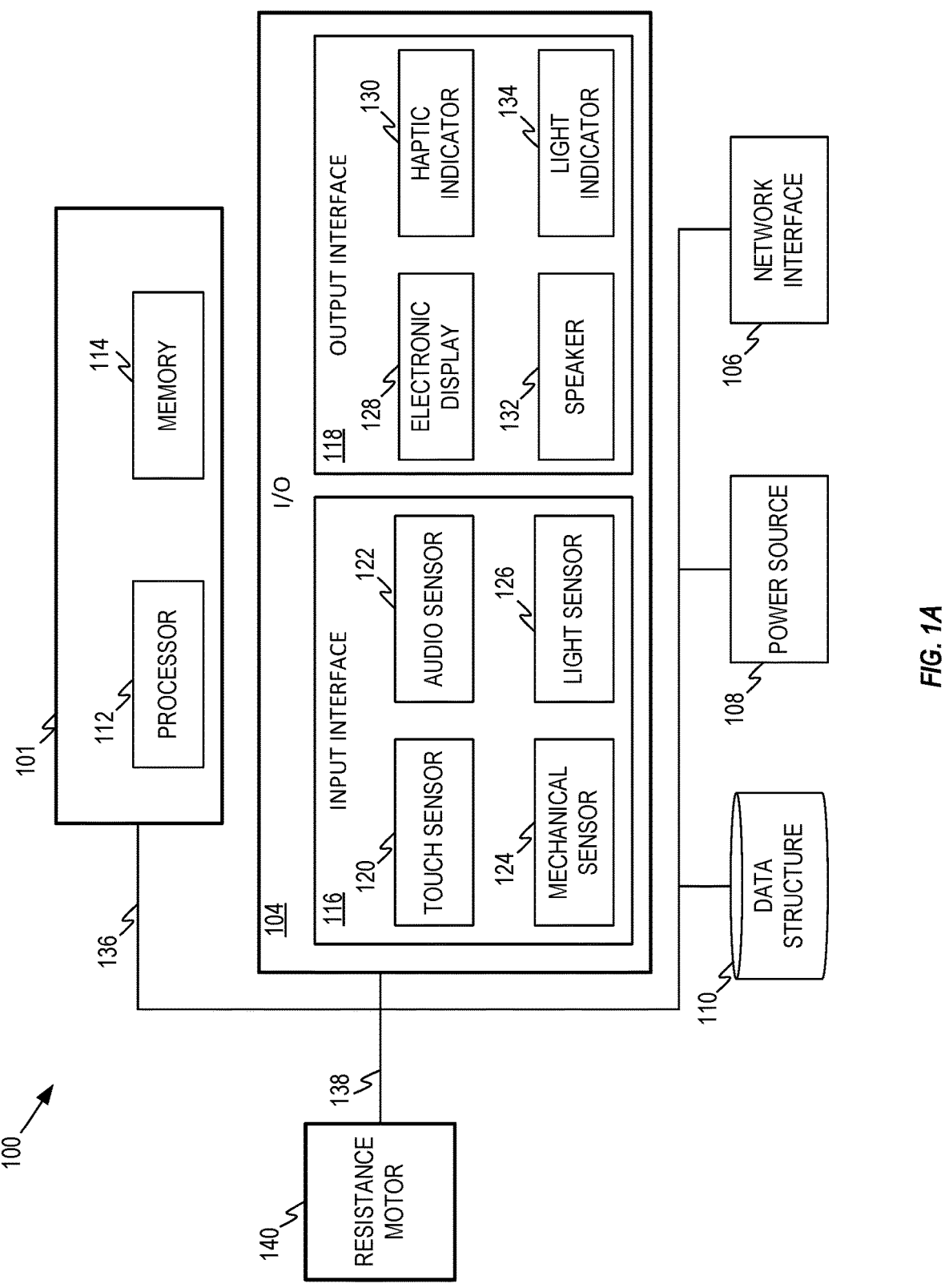
FIG. 1A is a schematic diagram of system architecture for an electronic exercise equipment including an electronic exercise machine, consistent with some embodiments of the present disclosure.

Disclosed herein are systems, methods, and non-transitory computer readable media relating to performance and adaptation of exercise routines, optionally using electronic exercise equipment such as electronic exercise machines. Some disclosed embodiments relate to software applications for using an electronic exercise machine. Some embodiments relate to operation of a modular electronic exercise machine, allowing integration of a plurality of individual electronic exercise machines. Some disclosed embodiments relate to performance of exercise routines. Some disclosed embodiments relate one or more combinations software applications, and/or operation of modular electronic exercise machines with associated mechanical features.

Some embodiments provide exercise equipment having a user interface allowing a user to adjust a time duration of a suggested/planned workout (e.g., to lengthen or shorten a workout) without changing the goal of the workout. The user may adjust the time duration before the workout starts, during the workout, or both. Some disclosed embodiments allow a user to shorten a workout while adapting the workout to meet the original goal via a software application that may adjust a remainder of a workout while meeting the goal.

For example, a user may plan a workout planned for 6 weeks to lose weight, with each workout lasting an hour. The user may need to change a particular workout during the 6-week period, by shortening a particular workout to 40 minutes. Based on the user's request, a controller (e.g., including at least one processor) may modify a workout to adapt to the shortened time while still meeting a goal of the workout. For example, a controller may change a number of repetitions and/or a resistance or intensity, and/or replace one or more exercises with different exercises to cause a similar exertion by the user as the original 1-hour workout. In some embodiments, the controller may user historical data relating to one or more previous workouts stored in memory to adjust a workout. In some embodiments, the method disclosed herein below may be used independent of a particular piece of exercise equipment.

Some embodiments involve a non-transitory computer readable medium containing instructions that when executed by at least one processor cause the at least one processor to perform adaptive exercise schedule modification operations. The at least one processor may initially access exercise-related data. For example, the exercise related data may be associated with an individual's past exercise history. The at least one processor may, based on the exercise-related data, control electronic exercise equipment (e.g., electronic exercise machine 200 shown in FIG. 2A) to initiate an exercise session of an initial predetermined duration. The exercise session may include a series of varied electronically controlled exercises selected to further an exercise goal. The at least one processor may receive input to modify the initial predetermined duration to an alternative duration. The received input may occur via a control on the exercise equipment. For instance, a user may provide input via a touch screen user interface associated with a dial (such as dial 216 shown in FIG. 2A), and/or via a mobile communications device paired to the exercise equipment. As another example, the at least one processor may receive input via a voice command.

The at least one processor may subsequently access the exercise-related data. The at least one processor may, based on the alternative duration, the exercise-related data, the record of the series, and the exercise goal, adjust the exercise session by altering a time of the exercise session and in a manner furthering the exercise goal, e.g., by maintaining the goal.

The at least one processor may receive input to modify the initial predetermined duration to an alternative duration while the exercise session of initial predetermined duration is in progress. The received input may be an instruction to shorten the initial predetermined duration. The at least one processor may adjust the exercise session by shortening one or more non-initiated exercises in a non-linear manner. The at least one processor may determine based on the subsequent access to the exercise related data that the individual requires more emphasis on a particular exercise than on another exercise. In such a case, adjusting may include allocating more remaining time to the particular exercise than to the other exercise. In some instances, the at least one processor may adjust by shortening at least one rest time between at least two of the series of varied electronically controlled exercises. The at least one processor may adjust a subsequent exercise regimen to account for the adjustment to the exercise session (e.g., to compensate for lost exercise to meet the goal). These embodiments are discussed in further detail below with respect to FIG. 5.

Some disclosed embodiments involve a cloud service configured to communicate with an electronic device and/or with an electronic exercise machine, e.g., allowing a user to participate in one or more pre-programmed exercise routines, and/or change one or more exercise routines. For example, a software application associated with a cloud service may be installed on a mobile communications device of a user. The software application may permit the cloud service to receive data from the user, and/or to provide recording, monitoring, tracking, and/or feedback services related to performances of exercise routines. In addition, the cloud service may communicate with a controller of an electronic exercise machine, allowing the cloud service to receive data from the electronic exercise machine. The cloud server may analyze data received from the mobile communications device and/or the electronic exercise machine, provide feedback, e.g., to modify one or more aspects of an exercise routine. Such modifications may include, for example, changing a timing, a frequency, a speed, an intensity, and/or a mode of one or more exercise routine (e.g., by making corresponding changes to a resistance of a resistance motor of the exercise machine), changing a height and/or angle of an arm of the exercise machine, switching an accessory connected to the arm, recommending a change of posture or position of the user, and/or make any other change to an exercise routine. In some embodiments, a cloud service may collect and analyze data unrelated to an exercise machine and associated with a user and/or user training aspects. In some applications, a cloud service may use data unrelated to an exercise machine and associated with a user and/or user training aspect to operate an electronic exercise machine.

For example, during a workout of a predefined length, a user may desire to shorten the workout. Rather than simply truncate the workout in progress, the cloud service may permit a user to modify the workout duration, e.g., by shortening the workout in a manner customized to the user, for example, in a manner to meet an exercise goal.

While a number of the foregoing examples are described in connection with a cloud service, similar functionality may be achieved with disclosed embodiments by incorporating the various functions into the exercise equipment itself, into software paired with the exercise equipment, or through networking with another device or server that aids in providing the associated functionality.

Various terms used in this detailed description and in the claims may be defined or summarized differently when discussed in connection with differing examples. It is to be understood that the definitions, summaries, and explanations of terminology in each instance apply to all instances, even when not repeated, unless the transitive definition, explanation or summary would result in inoperability of an embodiment.

Throughout, this disclosure mentions "disclosed embodiments," which refer to examples of inventive ideas, concepts, and/or manifestations described herein. Many related and unrelated embodiments and examples are described throughout this disclosure. The fact that some "disclosed embodiments" are described as exhibiting a feature or characteristic does not mean that other disclosed embodiments necessarily lack that feature or characteristic.

This disclosure employs open-ended permissive language, indicating for example, that some embodiments "may" employ, involve, or include specific features. The use of the term "may" and other open-ended terminology is intended to indicate that although not every embodiment may employ the specific disclosed feature, at least one embodiment employs the specific disclosed feature.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions, or modifications may be made to the components illustrated in the drawings, and the illustrative methods described herein may be modified by substituting, reordering, removing, or adding steps to the disclosed methods. Accordingly, the following detailed description is not limited to the specific embodiments and examples but is inclusive of general principles described herein and illustrated in the figures in addition to the general principles encompassed by the appended claims.

Some embodiments described herein involve an exercise machine. An exercise machine may refer to a mechanical device that may be used to perform physical exercise. Examples of exercise machines may include wall-mountable resistance devices, free standing resistance devices, treadmills, stationary bicycles, elliptical machines, weight machines, other resistance machines, and/or any other machine designed to engage a user in physical exercise.

Some disclosed embodiments involve an electronic exercise machine. An electronic exercise machine may refer to an exercise machine including a resistance motor associated with electronics for controlling the resistance. The electronics may control an amount of resistance applied during a weightlifting exercise by regulating, for example, a level, a frequency, a duration, a speed, a duty cycle, a range of motion, an exercise type, an operational mode, and/or any other attribute associated with resistance applied by a resistance motor. In some embodiments, electronics, including for example, at least one processor, may control force applied by a resistance motor in response to one or more user inputs.

In some embodiments, an electronic exercise machine may be associated with a user interface. Such a user interface may include one or more of an electronic display, a touch-sensitive screen, a microphone, a speaker, a haptic interface, a light emitting diode (LED), one or more adjustable dials, knobs, buttons, switches, and/or levers and/or any other type of manipulatable control enabling user inputs and/or information display. For example, a user may provide one or more inputs via a user interface associated with an electronic exercise machine to initiate, select, modify, share, and/or terminate an exercise routine. Such an interface may initiate signals to at least one processor associated with an electronic exercise machine. In a similar manner, the at least one processor may transmit one or more signals to convey information via a user interface to a user of an electronic exercise machine.

Some disclosed embodiments involve an electromagnet. An electromagnet may refer to a temporary magnet created by intermittent electrical currents. For example, an electromagnet may be formed by passing an electrical current through an electrically conductive wire wrapped around a piece of magnetic metal to produce an electromagnetic field. Some examples of electrically conductive wires may include copper, steel, and/or aluminum wires. Some examples of magnetic metal may include cast iron, wrought iron, galvanized steel, ferritic and martensitic stainless steel. The strength of an electromagnetic field produced by an electromagnet may be increased, decreased, or terminated by controlling a level of electrical current through the wire. Electromagnetic fields produced by one or more electromagnets may be used to introduce resistance to mechanical motion. Overcoming such resistance may require an application of a mechanical force.

Some disclosed embodiments involve a motor (e.g., a resistance motor). Such a motor may include a one or more electromagnets configured to apply a variable electromagnetic field as resistance. For example, a level of resistance produced by a resistance motor may correspond to an amount of weight (e.g., "digital weight") needed to be overcome by muscles during performance of a weight-bearing exercise. A resistance motor may be associated with at least one processor configured to control a level of electrical current flowing therethrough, allowing the at least one processor to control attributes associated with resistance or digital weight produced by the resistance motor. In some embodiments, a resistance motor may be associated with a lower bracket configured to connect a bottom end of a vertical wall-mountable beam to a wall. For example, a resistance motor may be located inside a housing configured as a lower bracket for connecting a vertical wall-mountable beam to a wall. A lower bracket may be made of durable metal, such as stainless or galvanized steel, or aluminum.

Some disclosed embodiments involve an electronic wall-mountable exercise machine. An electronic wall-mountable exercise machine may refer to an electronic exercise machine including a frame (e.g., a vertically wall-mountable beam) for attachment to a wall via a plurality of supporting brackets. The frame and brackets may be made of durable metal (e.g., steel and/or aluminum) for sturdiness and may support a pulley system, allowing a first end of a cable to be connected to a resistance motor and a second end of the cable to be connected to exercise equipment. In some embodiments, an electronic wall-mountable exercise machine may include a user interface (e.g., including one or more adjustable dials, knobs, buttons, switches, and/or levers) allowing interaction with a controller of the wall-mountable exercise machine, e.g., to receive feedback and/or customize a workout to meet a fitness level and/or goal. For example, a dial may allow adjusting a resistance of a resistance motor, and a button may allow changing a direction and/or mode for exerting a force on a cable.

Consistent with the present disclosure, a vertically wall-mountable beam or a vertically-mountable beam may include a pole, column, post, pillar, and/or any other elongated form configured for connection to a wall in a substantially vertical orientation. Such a structure may be made of metal (e.g., aluminum and/or steel), composite, high strength polymer, or any other material or combinations of materials sufficiently sturdy to withstand forces exerted during exercise.

Some embodiments involve a pair of tracks. A pair of tracks may include two parallel rails. Such rails may include, for example elongated bars with grooves running along the length of the bars). Each rail may provide a smooth and stable surface and at least one delimiting wall for guiding one or more wheels (e.g., of a trolley). The pair of rails, like the beam, may be made of a hard durable material, such as metal (e.g., steel, aluminum, or other alloys), composite, high strength polymer, or any other material or combinations of materials sufficiently sturdy to withstand forces exerted during usage. The rails may be integrally formed with the vertically-mountable beam or may be connectable to the beam. In some embodiments, a pair of tracks may be symmetric (e.g., each track of a pair of tracks may have substantially similar cross-sections). In some embodiments, a pair of tracks may be asymmetric (e.g., each track of a pair of tracks may have differing cross-sections). In some embodiments, one or both tracks of a pair of tracks may have an L-shaped cross-section (e.g., a single delimiting wall) for guiding one or more wheels of a trolley. In some embodiments, one or both tracks of a pair of tracks may have a U-shaped cross-section or a V-shaped cross-section (e.g., two delimiting walls) for guiding one or more wheels of a trolley. In some embodiments, one or both tracks of a pair of tracks may have a substantially circular or partially circular-shaped cross-section for guiding one or more wheels of a trolley. In some embodiments, a vertically wall-mountable beam may be manufactured via an extrusion process involving forcing a material through a pre-shaped die to produce a vertically wall-mountable beam including a pair of rails, e.g., from a single piece of metal.

Some disclosed embodiments may involve a cable. A cable may include a rope, cord, chain, belt, and/or any other band or cordage having a tensile strength for withstanding repeated applications of tension. A cable may include a plurality of fibers (e.g., stainless and/or galvanized steel) that may be combined and twisted to form an elongated structure, and may optionally include a coating such as nylon and/or PVC to reduce friction and wear. In some embodiments, a cable may have a tensile strength suitable for withstanding a resistance force associated with a resistance motor of an electronic exercise machine. For instance, a first end of a cable may connect to a resistive motor and a second end of the cable may connect to a moveable arm of an electronic exercise machine, allowing for a mechanical force applied to move the arm to be at least partially resisted by the resistive motor.

Some disclosed embodiments may involve a pulley or a pulley system. Either such term refers to a mechanical device including at least one wheel that acts to change the direction of a force applied to a cable circumscribing the wheel. The wheel may have a grooved edge or rim around which the cable passes. The pulley may be supported by a frame or shell (e.g., a block) for guiding a cable around the wheel such that rotation of the wheel may cause a direction of the cable to change (e.g., such that a downwards motion on one end of the cable may cause a corresponding upwards motion on the other end of the cable and the reverse). In some embodiments, a vertical wall-mountable beam may include a pulley located at an upper section thereof. A pulley of a vertical wall-mountable beam may be associated with an upper bracket configured to affix an upper end of the vertical wall-mountable beam to a wall. For example, a pulley may be located inside a housing configured as an upper bracket for connecting a vertical wall-mountable beam to a wall. The upper bracket may be made of durable metal, such as stainless or galvanized steel, or aluminum.

Some disclosed embodiments involve a trolley. A trolley may include a chassis or frame connected to at least one pair of wheels configured to roll along a rail or pair of rails (e.g., of a vertically wall-mountable beam associated with an electronic exercise machine). In some embodiments, a trolley may be associated with two pairs of wheels, three pairs of wheel, four pairs of wheels, or any other pluralities of sets of wheels. A trolley may include components made of metal, plastic, wood, resin, and/or any other stiff durable material. The trolley may be associated with a locking mechanism allowing the trolley to selectively lock at locations along a vertically wall-mountable beam of an electronic exercise machine. The trolley may be associated with an arm of an electronic exercise machine, such that moving the trolley along a rail or pair of rails of a vertically wall-mountable beam of the electronic exercise machine allows adjusting a height of the arm, and locking the trolley at a selected location allows fixing the height of the arm. In some embodiments, a trolley may include a catching mechanism (e.g., a loop or hook) for directing a cable, originating from the resistive motor to a proximal an of the arm of an electronic exercise machine via a pulley system. The cable may be fed through the arm and may exit a distal end of the arm where it may connect to an accessory, such that maneuvering the arm via the accessory exerts a tension on the cable, which may be at least partially resisted by the resistance motor.

Consistent with the present disclosure, an arm refers to an elongated structure. An arm of an exercise machine is an elongated structure that extends from the exercise machine to enable a user to apply exertions to the machine. In some embodiments, this may be enabled by a hollow within the arm for a cable associated with a pulley and connected to a resistance motor, such that exertion of a mechanical force via the cable (e.g., by a user of an electronic exercise machine exerting a force on the cable) may be at least partially resisted by the resistance motor. The arm of an electronic exercise machine may be adjustably associated with a vertically wall-mountable beam of the electronic exercise machine. For example, the arm may connect to a trolley configured to ride along a pair of tracks of a vertically wall-mountable beam, allowing adjustment to a height of the arm along the vertically wall-mountable beam by adjusting a location of the trolley along the pair of tracks. As another example, the arm may connect to a shoulder configure to rotate relative to a vertically wall-mountable beam of an electronic exercise machine, permitting adjustment to an angle of the arm relative the vertically wall-mountable beam through adjustment of an orientation of the shoulder.

Consistent with the present disclosure, a housing (e.g., motor housing) may include a rigid casing or enclosure encasement configured to protect equipment (e.g., a motor). A housing may be made of any durable material, such as metal, plastic, and/or resin. In some embodiments, a housing may include one or more vents, gaps, or holes to enable dissipation of heat. In some embodiments, a housing may include an opening therein for a power cable to connect to a power source (e.g., an electrical wall outlet and/or a battery).

Some disclosed embodiments include at least one processor. "At least one processor" may involve any physical device or group of devices having electric circuitry that performs a logic operation on an input or inputs. For example, the at least one processor may include one or more integrated circuits (IC), including an application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory. The memory may include a Random Access Memory (RAM), a Read-Only Memory (ROM), a hard disk, an optical disk, a magnetic medium, a flash memory, other permanent, fixed, or volatile memory, or any other mechanism capable of storing instructions. In some embodiments, the at least one processor may include more than one processor. Each processor may have a similar construction, or the processors may be of differing constructions that are electrically connected or disconnected from each other. For example, the processors may be separate circuits or integrated in a single circuit. When more than one processor is used, the processors may be configured to operate independently or collaboratively and may be co-located or located remotely from each other. The processors may be coupled electrically, magnetically, optically, acoustically, mechanically, or by other means that permit them to interact At least one processor may include a single processor or multiple processors communicatively linked to each other and capable of performing computations in a cooperative manner, such as to collectively perform a single task by dividing the task into subtasks and distributing the subtasks among the multiple processors, e.g., using a load balancer. In some embodiments, at least one processor may include multiple processors communicatively linked over a communications network (e.g., a local and/or remote communications network including wired and/or wireless communications links). The multiple linked processors may be configured to collectively perform computations in a distributed manner (e.g., as known in the art of distributed computing).

Some disclosed embodiments involve a non-transitory computer-readable medium or a memory. Such terms may refer to any type of physical memory on which information or data readable by at least one processor can be stored. Examples include Random Access Memory (RAM), Read-Only Memory (ROM), volatile memory, nonvolatile memory, hard drives, CD ROMs, DVDs, flash drives, disks, any other optical data storage medium, any physical medium with patterns of holes, markers, or other readable elements, a PROM, an EPROM, a FLASH-EPROM or any other flash memory, NVRAM, a cache, a register, any other memory chip or cartridge, and networked versions of the same. The terms "memory" and "computer-readable storage medium" may refer to multiple structures, such as a plurality of memories or computer-readable storage mediums located within a wearable device or at a remote location. Additionally, one or more computer-readable storage mediums can be utilized in implementing a computer-implemented method. Accordingly, the term computer-readable storage medium should be understood to include tangible items and exclude carrier waves and transient signals.

Some disclosed embodiments involve a touch sensor. A touch sensor may include any type of equipment that captures and records physical touch or contact. Touch sensors, for example, may be capacitive and/or may include one or more of complementary metal-oxide-semiconductor (CMOS) integrated circuit (IC) chips, an application-specific integrated circuit (ASIC) controller and a digital signal processor (DSP) for sensing pressure, temperature, humidity, and/or any other indicator of touch. A touch sensor may convert an indication of touch to an electronic signal, which may be transmitted to at least one processor.

Some disclosed embodiments involve an audio sensor. An audio sensor may include any device that detects sound waves and coverts the sound waves into at least one electrical signal. An audio sensor may include, for example, one or more microphones. Some examples of such microphones include, unidirectional microphones, bidirectional microphones, cardioid microphones, omnidirectional microphones, onboard microphones, wired microphones, wireless microphones, or any combination of the above. The electronic signals from an audio sensor may be transmitted to at least one processor.

Some disclosed embodiments involve a mechanical sensor. A mechanical sensor includes any device that detects some sort of mechanical deformation or movement and translates that detection into an electrical signal. A mechanical sensor may be associated with a mechanical interface (e.g., a button, key, ball, switch, lever, touch pad, or dial) such that applying a mechanical force on the mechanical interface may cause the mechanical sensor to transmit a signal to at least one processor.

Some disclosed embodiments involve a light sensor. A light sensor may be included any device or be capable of detecting and converting optical signals in the near-infrared, infrared, visible, and ultraviolet spectrums into electrical signals. Examples of light sensors include photodetectors, photosensors, digital cameras, semiconductor charge-coupled devices (CCDs), active pixel sensors in complementary metal-oxide semiconductor (CMOS), or N-type metal-oxide-semiconductor (NMOS, Live MOS). The electrical signals may be used to generate image data. Consistent with the present disclosure, the image data may include pixel data streams, digital images, digital video streams, data derived from captured images, and data that may be used to construct one or more 3D images, a sequence of 3D images, 3D videos, or a virtual 3D representation. A light sensor may convert an optic signal to an electronic signal, which may be transmitted to at least one processor.

Some disclosed embodiments involve an electronic display. An electronic display includes any device or element capable of generating a visible image from electrical signals. For example, an electronic display may include a screen (e.g., LCD or dot-matrix screen), an electroluminescent (EL) display, a liquid crystal display (LCD), light-emitting diode (LED)-backlit Liquid crystal display (LCD), a light-emitting diode (LED) display, an organic light-emitting diode (OLED) display, an active matrix organic light-emitting diode (AMOLED) display, a plasma (P) display, a quantum dot (QD) display, and/or any other type of technology for rendering information visually. At least one processor may transmit signals to an electronic display to cause information to be displayed visually.

Some disclosed embodiments involve a haptic indicator. A haptic indicator may include any element or device that outputs vibrations or forces detectable to a human when in contact with a portion of the human body, such as a finger or hand. A haptic indicator may include, for example, a vibrating motor, linear actuator, vibrational transducer, or any other force feedback device that provide tactile or haptic cues or that is capable of converting an electrical signal into corresponding vibrations or force applications. At least one processor may transmit signals to a haptic indicator to cause information to be rendered haptically.

Some disclosed embodiments involve a speaker. A speaker may include any element or device capable of outputting sound. For example, a speaker may include one or more transducers for converting electromagnetic waves into sound waves. At least one processor may transmit signals to a speaker to cause information to be rendered as sound.

Some disclosed embodiments involve a light indicator. A light indicator may include any element or device that emits light in order to convey information. (e.g., indicating that a machine is powered on, indicating a mode of operation, indicating proper or improper usage, or indicating any other information. A light indicator may include a single light source (e.g., an LED), an array of light sources, (e.g., an LED array associated with different colors). At least one processor may transmit signals to a light indicator to cause information to be rendered visually.

Some disclosed embodiments involve a data structure. A data structure may include any collection of data values and relationships among them. The data may be stored linearly, horizontally, hierarchically, relationally, non-relationally, uni-dimensionally, multidimensionally, operationally, in an ordered manner, in an unordered manner, in an object-oriented manner, in a centralized manner, in a decentralized manner, in a distributed manner, in a custom manner, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML database, an RDBMS database, an SQL database or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, and Neo4J. A data structure may be a component of the disclosed system or a remote computing component (e.g., a cloud-based data structure). Data in the data structure may be stored in contiguous or non-contiguous memory. Moreover, a data structure, as used herein, does not require information to be co-located. It may be distributed across multiple servers, for example, that may be owned or operated by the same or different entities. Thus, the term "data structure" as used herein in the singular is inclusive of plural data structures. A data structure may also include any hardware, software, firmware, or combination thereof for storing and facilitating the retrieval of information in the data structure.

Some disclosed embodiments involve a mobile communications device. A mobile communications device is a portable electronic instrument designed to facilitate information transmission to other devices or networks. Mobile communications devices may, for example, use cellular or other wireless and/or wired networks to transmit information such as voice and/or other data. For example, such transmissions may be in the form of voice calls, text messages, internet access, and application usage.

Mobile communications devices come in various forms, such as smartphones, tablets, laptop computers, IoT devices, wearable electronics (such as smart watches, smart rings, fitness trackers, smart glasses, smart clothing, smart jewelry, smart headphones, wearable digital assistants), and portable wireless hotspots. Depending on configuration and intended use, they may include features such as a touchscreen interface, a built-in camera, Wi-Fi, NFC, and/or Bluetooth connectivity, and GPS navigation.

Some disclosed embodiments involve a power source. A power source may include any element, device, or system for providing electrical energy to an electrical load or a circuit. Examples of power sources include one or more batteries (e.g., a lead-acid battery, a lithium-ion battery, a nickel-metal hydride battery, a nickel-cadmium battery), fuel cells, generators, capacitors, power converters, or connections (e.g., an electrical wall outlet) to an external source of electrical energy (e.g., an electric grid or other mechanism for supplying electricity). A power source may further include combinations of any of the foregoing.

Some disclosed embodiments involve a communications network. A communications network may include any type of physical or wireless infrastructure used to exchange data. For example, a communications network may be the Internet, a private data network, a virtual private network using a public network, a Wi-Fi network, a LAN or WAN network, a combination of one or more of the forgoing, and/or other suitable connections that may enable information exchange among or between various system components. In some embodiments, a communications network may include one or more physical links used to exchange data, such as Ethernet, coaxial cables, twisted pair cables, fiber optics, or any other suitable physical medium for exchanging data. A communications network may also include a public switched telephone network ("PSTN") and/or a wireless cellular network. A communications network may be secured or unsecured network. In other embodiments, one or more system components may communicate directly through a dedicated communications network. Direct communications may use any suitable technologies, including, for example, BLUETOOTH™, BLUETOOTH LE™ (BLE), Wi-Fi, near field communications (NFC), or other suitable communication methods that provide a medium for exchanging data and/or information between separate entities.

A communications network may include a plurality of nodes interconnected via network infrastructure allowing encoded information to flow therebetween. Such network infrastructure may include, for example, one or more routers, switches, boosters, cables (e.g., Ethernet, coaxial cables, twisted pair cables, fiber optics, wires, buses), antennae, and/or any other wired and/or wireless computer networking technology configured for exchanging data.

Some disclosed embodiments involve a network interface. A network interface may include electronic circuitry and/or software code enabling at least one processor to communicate with another processor or processors via a network according to a communications protocol (e.g., Transmission Control Protocol/Internet Protocol or TCP/IP). Such circuitry may include, for example, at least one processor, a memory, one or more antennae configured to send and/or receive wireless signals from other devices, one or more wires and/or cables configured to send and/or receive wired signals from other devices, a plurality of physical and/or virtual ports, one or more software interface layers for implementing one or more communications protocols (e.g., lower layer protocols such as TCP, User Datagram Protocol (UDP), IP, and Internet Control Message Protocol (ICMP), and application layer protocols, such as Hypertext Transfer Protocol (HTTP), Secure Socket Shell (SSH), Transport Layer Security (TLS), and Secure Sockets Layer (SSL), and/or any other component required to enable networked communication between a plurality of computing devices.

Some disclosed embodiments involve a cloud service. A cloud service is a product that enables access to computing resources, such as servers, storage, and applications, over a network such as the internet. Cloud services are typically provided by third-party vendors who manage and maintain the underlying infrastructure allowing users to access and use the services via the internet. Non-limiting examples of types of cloud services, include Infrastructure as a Service (IaaS), Platform as a Service (PaaS), and Software as a Service (Saas). In some embodiments, a cloud service may execute program code instructions to implement one or more virtual machines.

In some embodiments, a communications network may be associated with a client-server model, allowing a cloud service to provide data storage and/or computational services to one or more client devices via the communications network. For example, a cloud service may store data and software associated with one or more electronic exercise machines and/or mobile communications devices (e.g., client devices) and/or execute program code instructions associated with using one or more electronic exercise machines. For example, a cloud server may store data and/or execute program code instructions for implementing a plurality of operational modes for an electronic exercise machine (e.g., in association with one or more exercise routines), creating an interface between a mobile communications device and one or more electronic exercise machines, and/or pairing two or more modular electronic exercise machines.

As another example, a cloud server may store data and execute program code instructions associated with performances of exercise routines (e.g., with or without an electronic exercise machine). For example, a cloud server may store results or achievements and/or provide feedback associated with performances of exercise routines (e.g., by a single or by multiple users), provide instructions for using an electronic exercise machine and/or for implementing differing modes of operation of an electronic exercise machine, facilitate interactions between remote users performing exercise routines (e.g., with or without an electronic exercise machine), and/or provide any other service associated with performances of exercise routines.

Some disclosed embodiments may involve signals. Signals may refer to an electrical or electromagnetic wave that carries information such as voice, video, or data. Signals can take various forms, including analog signals and digital signals. Other signal examples include radio signals, optical signals, microwave signals, infrared signals, ultrasonic signals, or any other wave or other conveyance that carries information. Non-limiting examples of signals include signals in the electromagnetic radiation spectrum (e.g., AM or FM radio, Wi-Fi, Bluetooth, radar, visible light, lidar, IR, Zigbee, Z-wave, and/or GPS signals), sound or ultrasonic signals, electrical signals (e.g., voltage, current, or electrical charge signals), electronic signals (e.g., as digital data), tactile signals (e.g., touch), and/or any other type of information encoded for transmission between two entities via a physical medium.

Some disclosed embodiments involve an indication. An indication may include a measurement, sign, and/or a signal conveying information about a state and/or level of a physical phenomenon. For example, an indication may signal the presence, occurrence, or status of something. An indication may be provided in a form that can be detected by a person or a system. For example, computers or other electronics may detect indications through signals, and humans may detect indications through light, audio, haptics, odor, or taste. In some instances, electronic sensors can also detect indications through light, audio, haptics, and odor, as well as through substance or image sensing.

Some disclosed embodiments may involve a mode of operation. A mode of operation refers to a way in which something works. For example, a device or system may work in a number of different ways, depending on a mode selection. A mode of operation may, by way of example, refer to a manner and/or a set of conditions for performing one or more procedures. A mode of operation may tune or adjust an operation of a system to accommodate a particular set or range of conditions. For instance, a first mode of operation may be associated with a first set of conditions and a second mode of operations may be associated with a second set of conditions, where the first mode of operation may be incompatible with the second set of conditions, and the second mode of operation may be incompatible with the first set of conditions. However, modes need not be incompatible. In some instances, a mode reflects a use preference, and the mode may be changed when preferences change.

FIG. 1A is a block diagram of exemplary system architecture of an electronic exercise machine, consistent with some embodiments of the present disclosure. It is to be noted that FIG. 1A is a representation of just one embodiment, and it is to be understood that some illustrated elements might be omitted, and others added within the scope of this disclosure. For example, some elements of FIG. 1A may be grouped and/or housed separately. In some embodiments, circuitry associated with a resistance motor of an electronic exercise machine may be housed and/or positioned separately from at least one processor configured to control settings for operating the electronic exercise machine (e.g., a control unit may be located in proximity to a resistance motor and at least one processor may be located elsewhere, and may be in electronic communication with the control unit). While housed and/or located separately, the control unit and the at least one processor may be in communication via wired and/or wireless means. For example, a user may set a desired resistance weight via a software application installed on a mobile communications device. The mobile communications device may transmit an indication of the desired resistance weight to at least one processor. Based on the indication, the at least one processor may transmit a control signal to the control unit to cause the resistance motor to apply the desired resistance weight.

System architecture 100 may include a control circuit 101, an I/O (input-output) unit 104, a network interface 106, a power source 108, and a data structure 110. Control circuit 101 may include at least one processor 112 and a memory 114. I/O unit 104 may include an input interface 116 and an output interface 118. Input interface 116 may include one or more of a touch sensor 120, an audio sensor 122, a mechanical sensor 124, and a light sensor 126, and/or any other type of sensor configured to receive an input. Output interface 118 may include one or more of an electronic display 128, a haptic indicator 130, a speaker 132, one or more light indicators 134, and/or any other type of output interface. Control circuit 101, I/O unit 104, network interface 106, power source 108, and data structure 110 may be interconnected via bus system 136. Control circuit 101 may be connected to a resistance motor 140 via one or more wires and/or cables 138. In some embodiments, one or more components of control circuit 101 may be located inside a housing encasing resistance motor 140, however this is not required.

For example, upon receiving a selection of an exercise routine to be performed using an electronic exercise machine via input interface 116, at least one processor 112 may retrieve data from memory 114 associated with the selected exercise routine. Such data may include, for instance, settings, preferences, a history of prior performances of the selected exercise routine, and/or any other data associated with the selected exercise routine. The at least one processor 112 may apply the retrieved data to control a current supplied to resistance motor 140, to thereby control the resistance applied by resistance motor 140 during performance of the selected exercise routine.

Figure 1B:
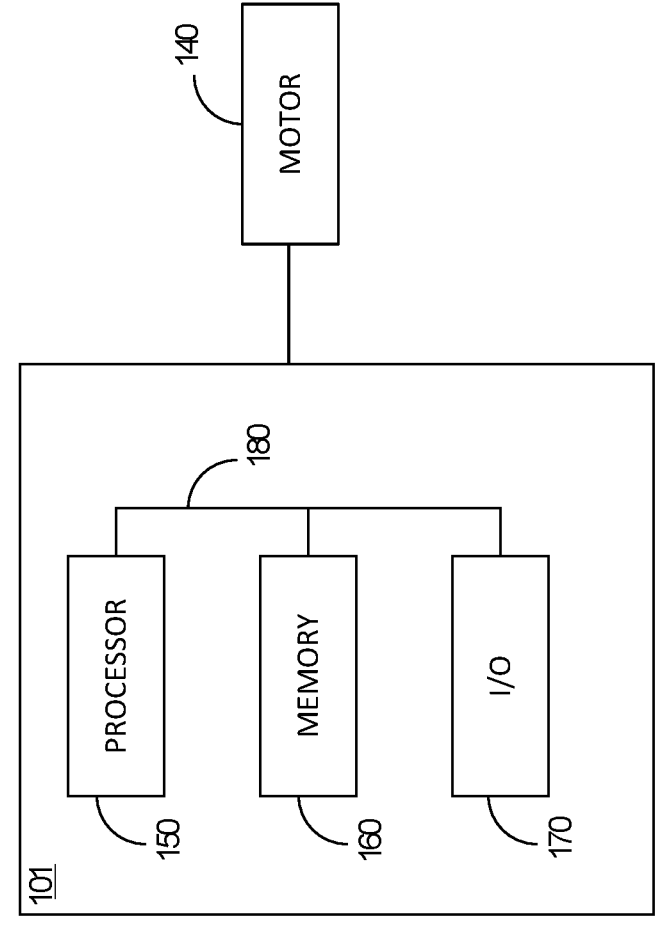
FIG. 1B is a block diagram of a controller for controlling an electronic exercise machine, consistent with some embodiments of the present disclosure.

FIG. 1B is a block diagram of a controller for controlling an electronic exercise machine, consistent with some embodiments of the present disclosure. Components of FIG. 1B may be similar in description to the corresponding components of FIG. 1A. A controller 101 of electronic exercise equipment 200 may include at least one processor 150, at least one memory 160, and an input output (I/O) 170 connected via a bus system 180. I/O 170 may include wired and/or wireless (e.g., one or more antennas) communications means enabling electronic communication between at least one processor 150 and another processor and/or device via a communications network. For instance, at least one processor 150 may communicate with mobile communications device 224 and/or another at least one processor 150 configured with another instance of electronic exercise equipment 200 (e.g., see FIG. 2E showing paired electronic exercise equipment 200A and 200B) via a pairing interface such as I/O 170. In some embodiments, at least one processor 150 may communicate with a wearable extended reality appliance via I/O 170. Some or all of controller 101 may be located within a motor housing 140, while some elements such as at least one processor 150, at least one memory 160, input output (I/O) 170), a bus system 180 may be encased within other portions of the equipment.

Figure 2A:
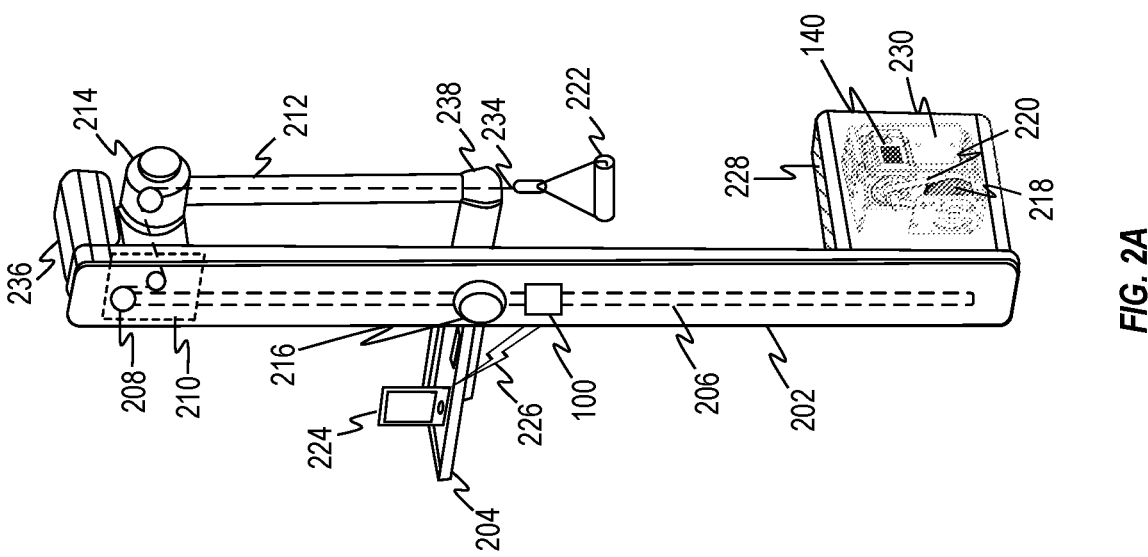
FIG. 2A is a perspective view of an exemplary wall-mountable electronic exercise machine, consistent with some embodiments of the present disclosure.
Figure 2A:
Figure 2C:
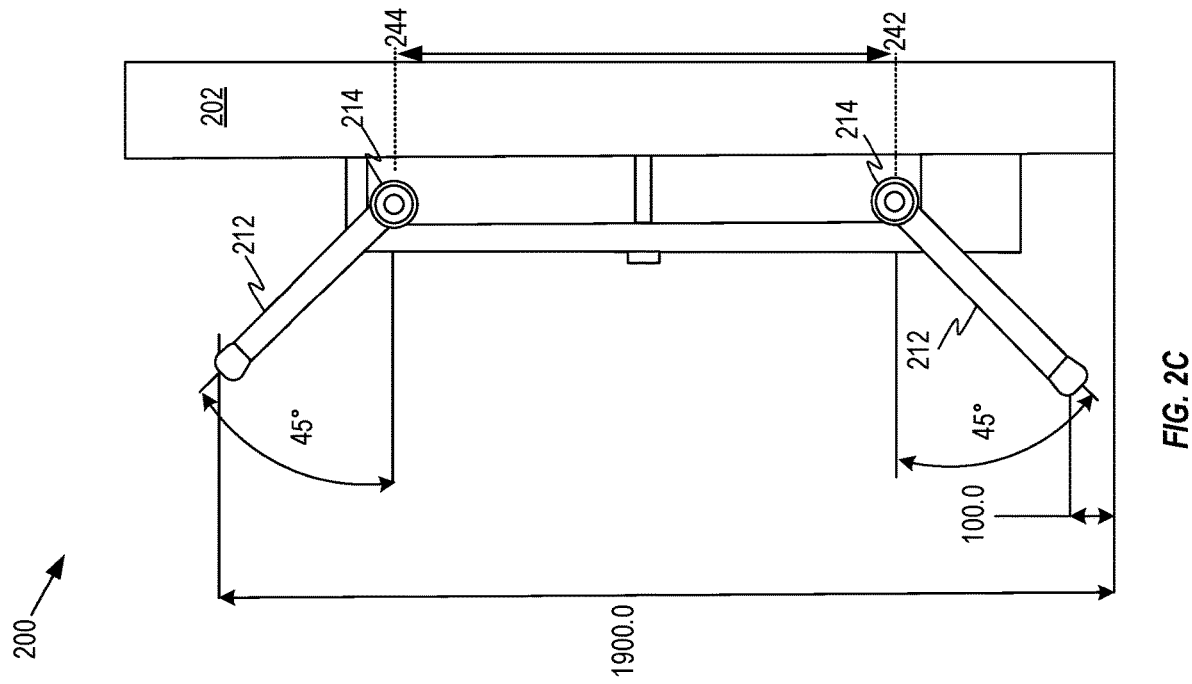
FIG. 2C is another side view of the exemplary wall-mountable electronic exercise machine of FIG. 2A, showing two extreme trolley and arm positions, consistent with some embodiments of the present disclosure.

FIG. 2A is a perspective view of an exemplary wall-mountable electronic exercise machine 200, consistent with some embodiments of the present disclosure. Wall-mountable electronic exercise machine 200 may include a vertically wall-mountable beam 202 connected to a T-bar 204, resistance motor 140, control circuit 101 (e.g., see FIG. 1B) or a controller (not shown in FIG. 2A), a cable 206, a pulley system 208, a trolley 210, an arm 212, a rotatable shoulder 214, and a control knob or dial 216. Resistance motor 140 may be located towards a base of vertically wall-mountable beam 202, however this is not required. Resistance motor 140 may be housed inside a housing 228 including a bracket 230 (e.g., a lower bracket) for attaching to a lower section of wall 232. Vertically wall-mountable beam 202 may include an upper bracket 236 for attaching to an upper section of wall 232.

In some embodiments, T-bar 204 may include a bracket and a shelf. The bracket may be configured to attach to the wall and to vertically wall-mountable beam 202 and the shelf may be configured to cover the bracket and support one or more accessories (e.g., a cellular phone, a water bottle, and/or any other accessory.) As an example, a width of vertically wall-mountable beam 202 may be approximately 130 mm, a distance from a base of vertically wall-mountable beam 202 and T-bar 204 may be approximately 806 mm, and a length of T-bar 204 may be approximately 322 mm.

Pulley system 208 may be located towards a top of vertically wall-mountable beam 202. Resistance motor 140 may be connected to a spool 218 via a belt 220. Cable 206 may extend from spool 218, running substantially along the length of vertically wall-mountable beam 202, through pulley system 208, to trolley 210 and rotatable shoulder 214 through arm 212, exiting from a wrist 238 to connect to an exercise accessory 222 connected thereto, such that a pulling force applied to exercise accessory 222 may be at least partially resisted by resistance motor 140 via cable 206. Trolley 210 may be configured to move along the length of vertically wall-mountable beam 202 and lock at differing heights, allowing to adjust a height of arm 212, as described in greater detail herein. Rotatable shoulder 214 may allow adjusting an angle of arm 212 relative to vertically wall-mountable beam 202, as described in greater detail herein. At least one processor 112 of control circuit 101 may transmit one or more signals to control a level of current flowing through resistance motor 140, thereby controlling a level of resistance applied by resistance motor 140 onto cable 206.

A control knob such as dial 216 may provide a user interface allowing a user to engage in electronic communication with wall-mountable electronic exercise machine 200. Dial 216 may be associated with I/O unit 104. For example, a user may use dial 216 to adjust one or more operational parameters and/or attributes associated with a resistance applied by resistance motor 140 onto cable 206. At least one processor 112 of control circuit 101 may receive an indication of an attribute selection via dial 216 from I/O 104 and may transmit a signal causing an adjustment to a current or a voltage flowing to resistance motor 140, to thereby cause resistance motor 140 to apply resistance characterized by the selected attributes to cable 206.

In some embodiments, control circuit 101 may pair to a mobile communications device 224 via network interface 106 (e.g., see FIG. 1A) to establish a (e.g., wireless) communications channel 226. Mobile communications device 224 may be configured with a user interface associated with wall-mountable electronic exercise machine 200, allowing a user to engage in electronic communication with at least one processor 112 of wall-mountable electronic exercise machine 200 via communications channel 226. For example, a user may use mobile communications device 224 to adjust a resistance and/or receive an indication of resistance applied by resistance motor 140 onto cable 206, change a mode of operation wall-mountable electronic exercise machine 200, receive updates and/or a report associated with an exercise routine performed using wall-mountable electronic exercise machine 200, as described in greater detail herein.

In some embodiments, an electronic exercise machine and/or a paired mobile communications device may communicate with an associated cloud service via a communications network. For example, the cloud service may include a server and a data structure configured to provide data and/or processing services associated with operating an electronic exercise machine, and/or for with performances of one or more exercise routines (e.g., with or without an electronic exercise machine).

Figure 2B:
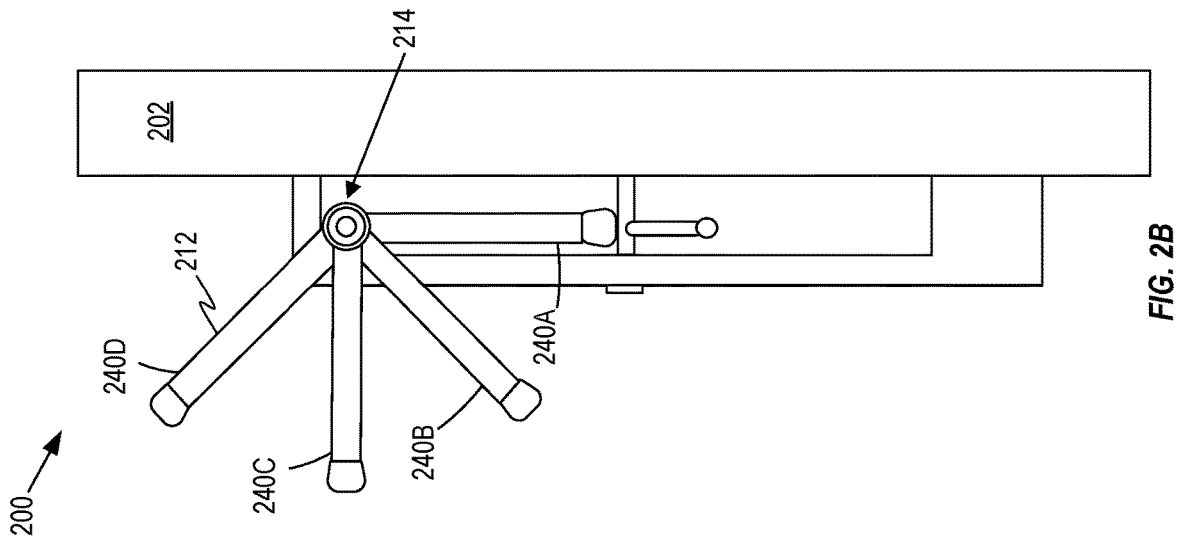
FIG. 2B is a side view of the exemplary wall-mountable electronic exercise machine of FIG. 2A, showing various arm positions, consistent with some embodiments of the present disclosure.

FIG. 2B is a side view of exemplary wall-mountable electronic exercise machine 202 of FIG. 2A, consistent with some embodiments of the present disclosure. Rotatable shoulder 214 may allow adjusting an angle of arm 212 relative to vertically wall-mountable beam 202 in four differing orientations, 240A, 240B, 240C, and 240D. Orientation 240A may be substantially parallel to vertically wall-mountable beam 202. Orientation 240B may be substantially at a 45° angle to vertically wall-mountable beam 202. Orientation 240c may be substantially perpendicular to vertically wall-mountable beam 202 (e.g., and substantially parallel to a floor). Orientation 240D may be substantially at a 135° angle to vertically wall-mountable beam 202. While four different orientations are shown, this does not limit this disclosure, and arm 212 may be oriented at greater than four, or less than four orientations.

FIG. 2C is another side view of exemplary wall-mountable electronic exercise 202 machine of FIG. 2A, showing arm 212 selectively positioned at two differing heights, 242 and 244, consistent with some embodiments of the present disclosure. Trolley 210 (see FIG. 2A) may slide along vertically wall-mountable beam 202 to position rotatable shoulder 214 and arm 212 at heights 242 and 244. While only two different heights are shown, this does not limit the disclosure, and arm 212 may be selectively positioned at more than two different heights along vertically wall-mountable beam 202. In some embodiments, arm 212 may be selectively positioned at ten different heights along vertically wall-mountable beam 202 (e.g., spaced 10 cm apart).

Figure 2D:
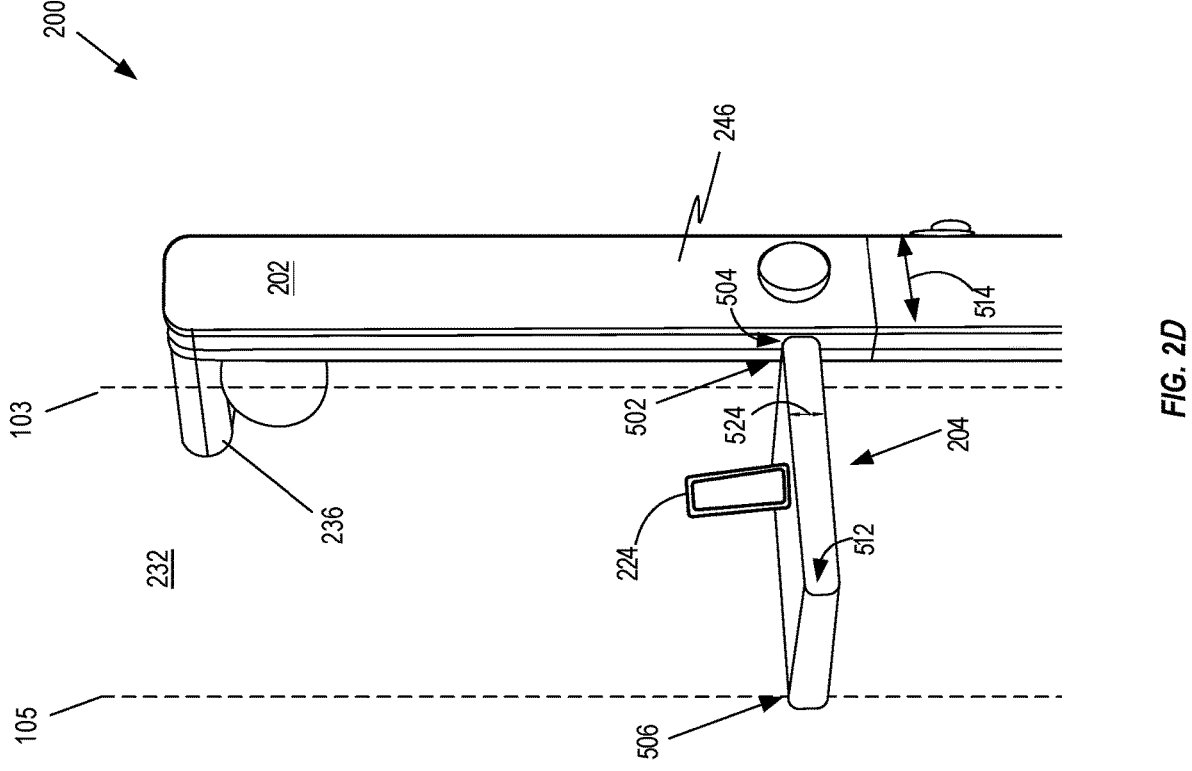
FIG. 2D is another perspective view of the exemplary wall-mountable electronic exercise machine of FIG. 2A, illustrating positioning relative to wall studs, consistent with some embodiments of the present disclosure.
Figure 2E:
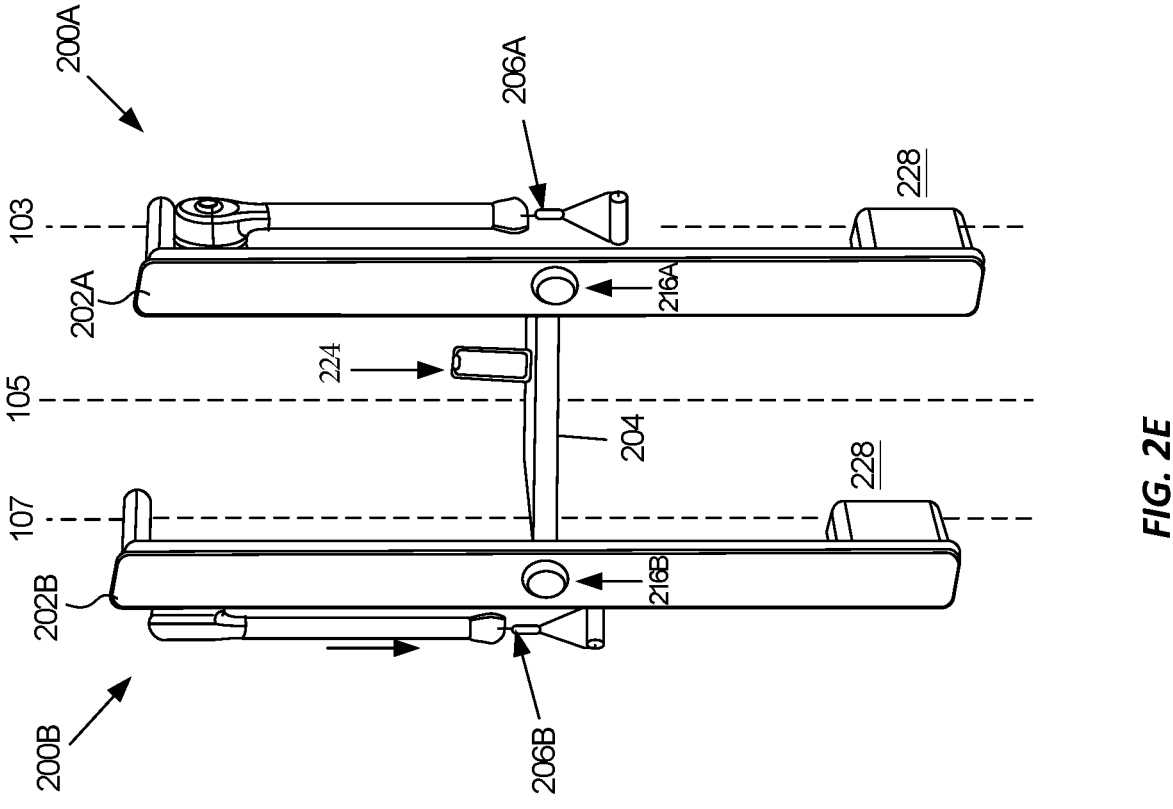
FIG. 2E is a perspective view of electronic exercise equipment illustrating positioning relative to wall studs, consistent with some embodiments of the present disclosure.

Reference is now made to FIG. 2D, which illustrates an exemplary T-bar 204 connected to vertically wall-mountable beam 102, consistent with some disclosed embodiments. T-bar 204 may have a first end 502 configured to connect to an intermediate portion 504 of vertically wall-mountable beam 202 and a second end 506 configured for connection to second stud 105 spaced from first stud 103 in the wall 232 (e.g., both shown indicated by dashed centerline lines). Connecting T-bar 204 thus may thereby resist the torque component of the exercise force, e.g., which may otherwise be exerted on vertically wall-mountable beam 202 and which would otherwise tend to pull vertically wall-mountable beam 202 out of wall 232. T-bar 204 may be oriented horizontally, perpendicular to vertically wall-mountable beam 202 such T-bar 204 connected to vertically wall-mountable beam 202 at intermediate portion 504 may form a "T" shape rotated by 90°. In some embodiments, T-bar 204 may be connectable to vertically wall-mountable beam 202 at a mid-location on vertically wall-mountable beam 202 (e.g., between upper bracket 236 and lower bracket 230).

In some embodiments, T-bar 204 may be configured as a shelf. In some embodiments, a shelf may attach to T-bar 204, the shelf may be shorter that T-bar 204. For instance, the shelf may be configured to hold a mobile communications device 224 such as a cell phone in an upright position, a bottle of water, a towel, and the like. In some embodiments, the shelf may include a phone charger integrated therewith, allowing mobile communications device 224 to be charged during an exercise session. The shelf may include hooks or other connectors thereon to permit accessories (e.g., various handles) to be stored thereon. In some embodiments, vertically wall-mountable beam 202 may include a faceplate 246 thereon (e.g., as an esthetic cover that may be suited to a living space in a home), where a height 524 of an edge 512 of the shelf may be narrower than a width 514 of the faceplate 246 of wall-mountable beam 202. For instance, these dimensions may give electronic exercise equipment 200 a sleek and esthetic appearance for a home gym.

Reference is made to FIG. 2E illustrating an exemplary configuration for two paired units of electronic exercise equipment 200A and 200B, consistent with some disclosed embodiments. Electronic exercise equipment 200A and 200B may correspond to electronic exercise equipment 200 of FIG. 2D. FIG. 2E illustrates three wall studs 103, 105, and 107, indicated as dashed lines. In some embodiments, T-bar 204 may be configured to extend between and connect to an additional vertically wall-mountable beam 202B mounted on a third stud 107 adjacent to second stud 105 and on a side of the second stud 105 opposite the first stud 103. In some embodiments, vertically wall-mountable beam 202A, the additional vertically wall-mountable beam 202B, and the T-bar 204 cooperate for form an H-configuration, with the T-bar 204 configured to resist torquing of both the vertically wall-mountable beam 202A and the additional vertically wall-mountable beam 202B.

FIG. 2E shows devices 200A and 200B each comprised of a vertical beam and joined by a single T-bar in an H-configuration (i.e., the T-bar of a single device becomes an H-bar when two devices share the T-bar).

Figure 2F:
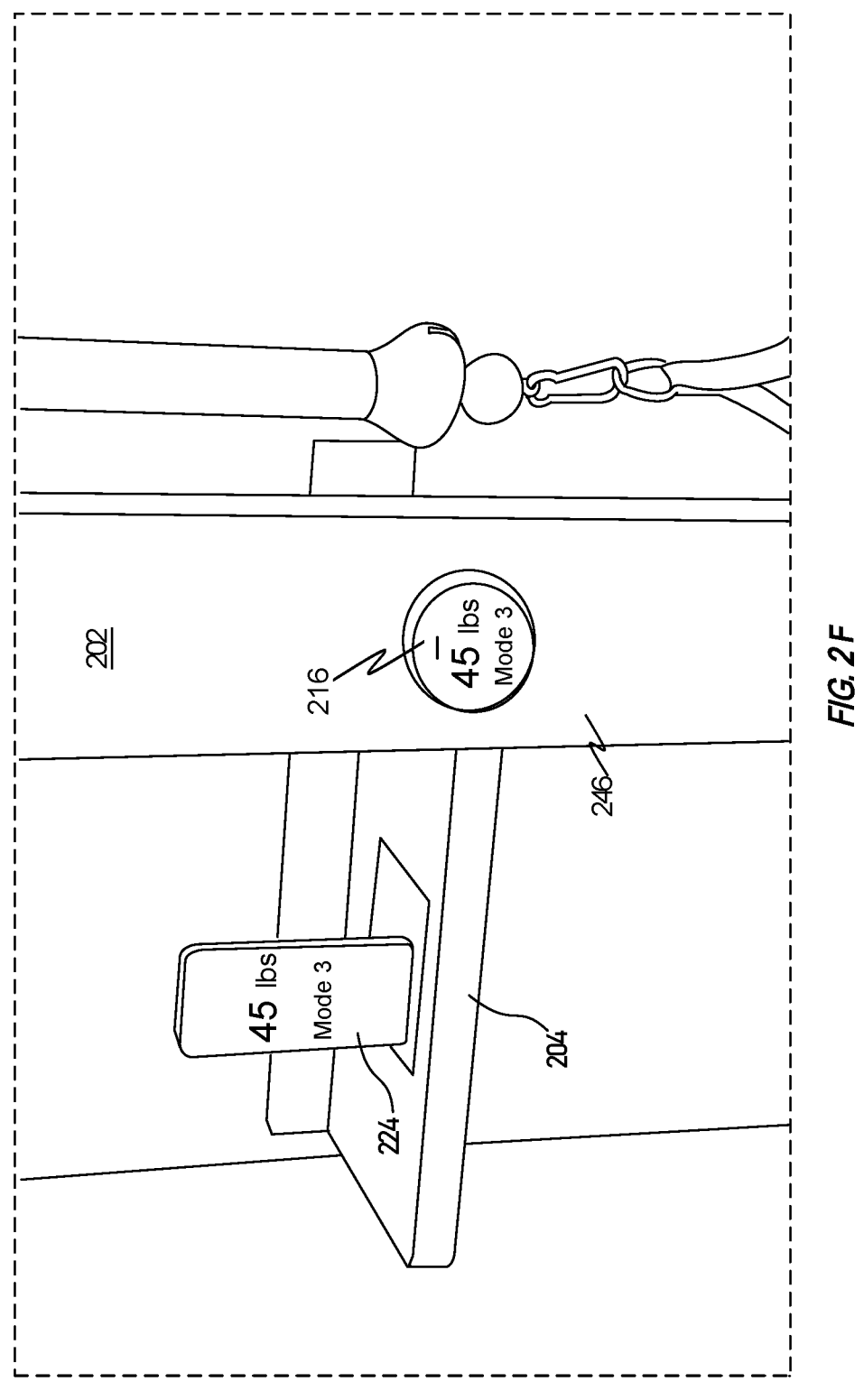
FIG. 2F is a perspective view of a portion of an exemplary wall-mountable electronic exercise machine in use with a paired cell phone, consistent with some embodiments of the present disclosure.
Figure 2G:
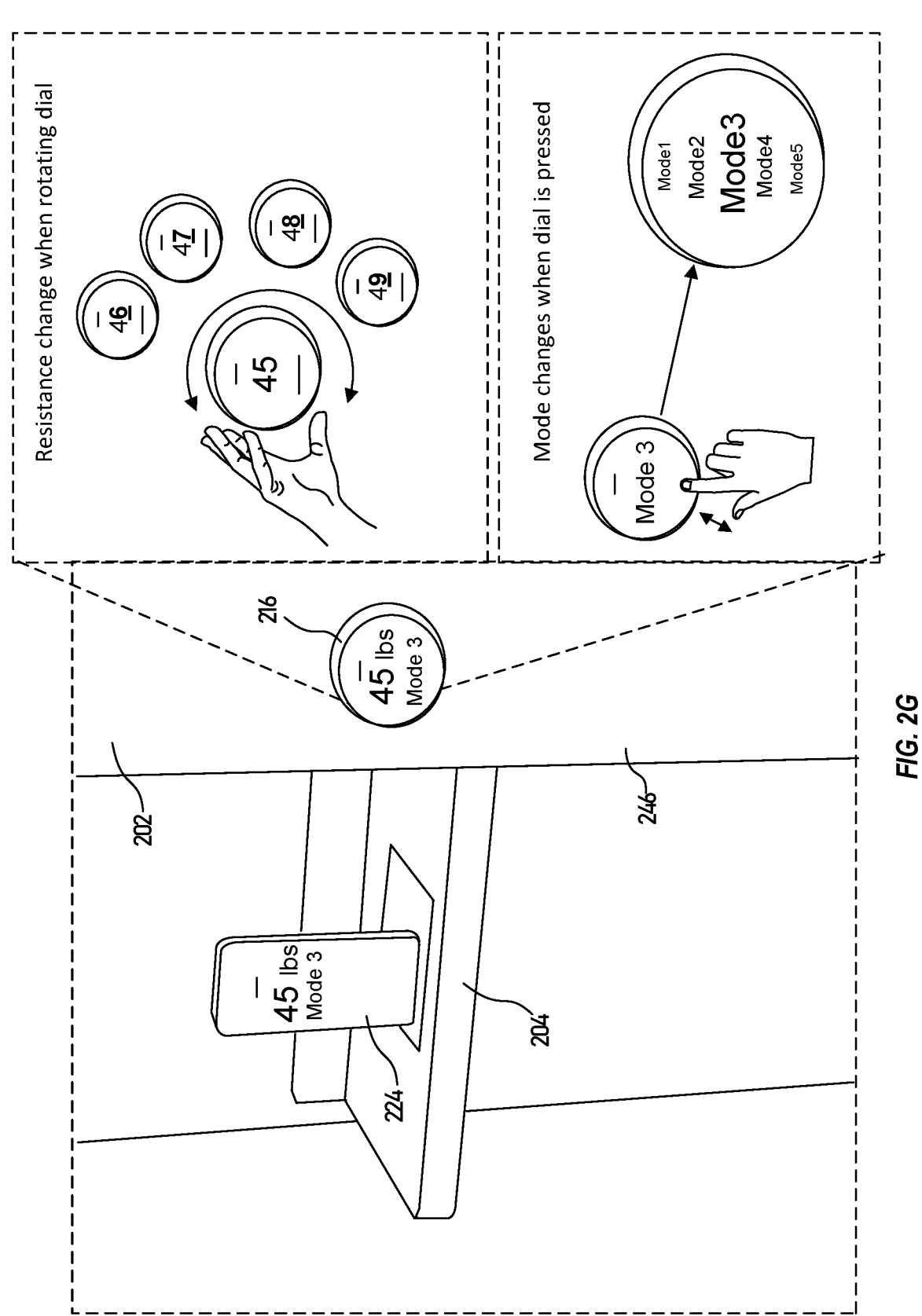
FIG. 2G include close-up perspective views of user interfaces including dial functions of an electronic exercise machine, consistent with some embodiments of the present disclosure.

Reference is made to FIG. 2F illustrating an exemplary dial 216 for electronic exercise equipment 200, consistent with some disclosed embodiments. In some embodiments, electronic exercise equipment 200 may include a dial 216 mounted on faceplate 246 of vertically wall-mountable beam 202. Dial 216 may be aligned with a connection location of T-bar 204. In some embodiments, dial 216 may function as a user interface for electronic exercise equipment 200, for controlling the resistance, selecting modes of operation, and/or control an operation of vertically wall-mountable beam 202.

Figure 3:
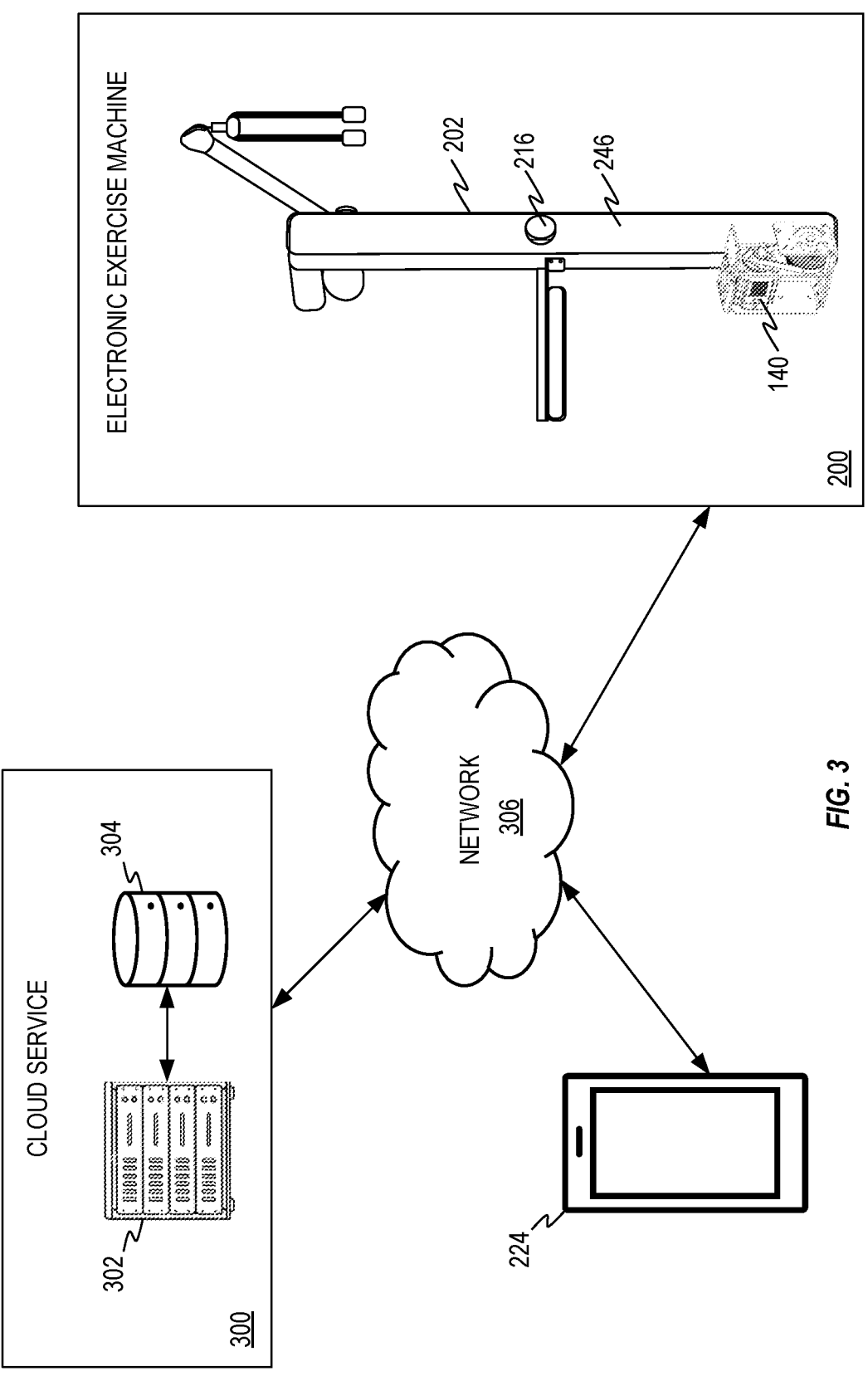
FIG. 3 is a schematic network diagram, consistent with some embodiments of the present disclosure.

FIG. 3 is a schematic illustration of a cloud service 300 associated with wall-mountable electronic exercise machine 200, consistent with some embodiments of the present disclosure. Cloud service 300 includes at least one server 302 (e.g., including at least one processor), and a data structure 304 connected to a communications network 306. Cloud service 300, wall-mountable electronic exercise machine 200 and mobile communications device 224 may communicate via a communications network 306. In some embodiments, communications network 306 may include a dedicated communications network, such as a Bluetooth communications channel connection mobile communications device 224 with at least one processor 112 of electronic exercise machine 200. In some embodiments, a light sensor (e.g., a camera) associated with mobile communications device 224 may capture images (e.g., of a user performing an exercise routine with or without wall-mountable electronic exercise machine 200). Cloud service 300 may store and analyze the images or videos, for example, to allow a first user of a first instance of wall-mountable electronic exercise machine 200 compete with a second user (e.g., of a second instance of wall-mountable electronic exercise machine 200), to provide feedback and/or instructions to a user performing an exercise routine, and/or provide any other service associated with performances of exercise routines (e.g., with or without wall-mountable electronic exercise machine 200).

Figure 4:
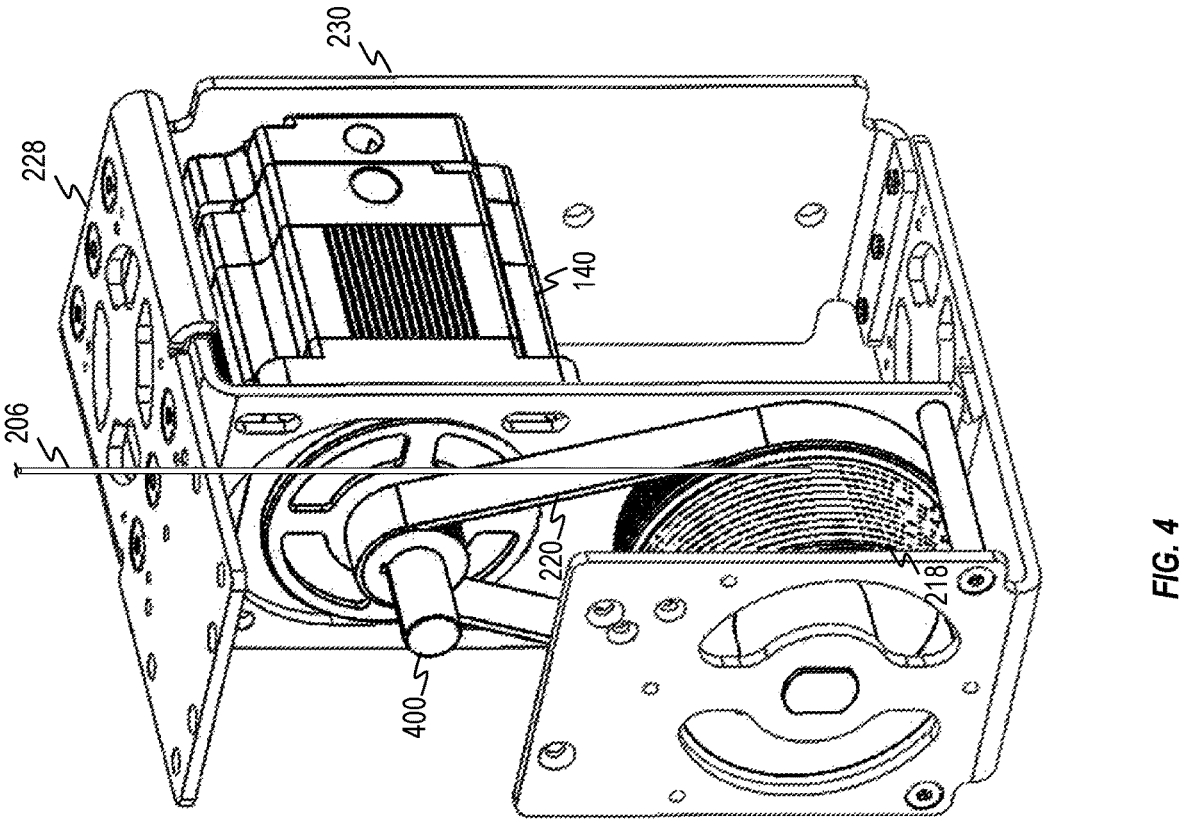
FIG. 4 is a perspective view of an exemplary resistance motor, spool, partial housing and mounting bracket of a wall-mountable electronic exercise machine, consistent with some embodiments of the present disclosure.

FIG. 4 is an illustration of exemplary resistance motor 140 of wall-mountable electronic exercise machine 200, consistent with some embodiments of the present disclosure. Resistance motor 140 may be housed in housing 228 connected to wall-mountable electronic exercise machine 200. In some embodiments, housing 228 may be located at a base of wall-mountable electronic exercise machine 200. Housing 228 may include a bracket 230 (e.g., a lower bracket) for connect housing 228 to wall 232, thereby connecting a first (e.g., lower) end of wall-mountable electronic exercise machine 200 to wall 232. For example, bracket 230 may connect to wall 232 using one or more screws, bolts, anchors, washers, clips, and/or hooks.

Resistance motor 140 may include wiring connected to a power source (not shown) for carrying an electrical current, one or more permanent magnets (also not shown), and an axle 400. In response to a current flowing through the wiring of resistance motor 140, the one or more permanent magnets of resistance motor 140 may produce a magnetic resistance (e.g., impedance) resisting a rotation of axle 400. A magnetic resistance imposed on axle 400 by resistance motor 140 may have characteristics corresponding to characteristics of a current flowing through the wiring of resistance motor 140. Such characteristics may include, for example, an amplitude, a frequency, a phase, a timing (e.g., on/off), a direction, and/or any other characteristic of an electrical and/or an electromagnetic signal. At least one processor 112 (e.g., see FIG. 1) may control characteristics of a current or voltage flowing through the wiring to thereby control characteristics of the magnetic resistance produced by resistance motor 140 and resisting a rotation of axle 400.

In FIG. 4, belt 220 may wrap around axle 400 and spool 218 to thereby connect spool 218 to axle 400 of resistance motor 140. A first end of cable 206 may be fastened to spool 218, and a first length of cable 206 may be wound around spool 218. A second length of cable 206 may run through wall-mountable electronic exercise machine 200, through pulley system 208, and exit from a distal end of arm 212. A second end 234 of cable 206 may exit from arm 212 and may be connected to exercise accessory 222, such that manipulating exercise accessory 222 may pull on cable 206, and impose a rotational force (e.g., a torque) on spool 218 and axle 400 via belt 220. The torque imposed on spool 218 by manipulating exercise accessory 222 may be at least partially resisted by axle 400 due to the magnetic resistance produced by resistance motor 140.

Some disclosed embodiments involve an adaptive exercise schedule modification. An adaptive schedule may include a flexible or dynamic plan or program that can adjust and adapt based on changing circumstances, priorities, or requirements. It is designed to accommodate unforeseen events, shifting priorities, or the need for additional flexibility in a routine or plan. A modification refers to a change or an ability to change. For example, a schedule may be considered adaptive if, after its creation, one or more aspects of the schedule may be changed. In the context of an exercise schedule, for example, an adaptive schedule modification may involve a change in a routine or a plan. A particular exercise that was part of schedule may be eliminated, shortened, lengthened, modified (such as through the addition or subtraction of resistance), or replaced with another exercise or a variation in directions. The schedule may further be adaptive through a rearrangement of an order of exercises in the routine, an elimination or addition of time between exercises or repetitions, and/or through adjustment of the overall duration of the schedule.

Figure 5:
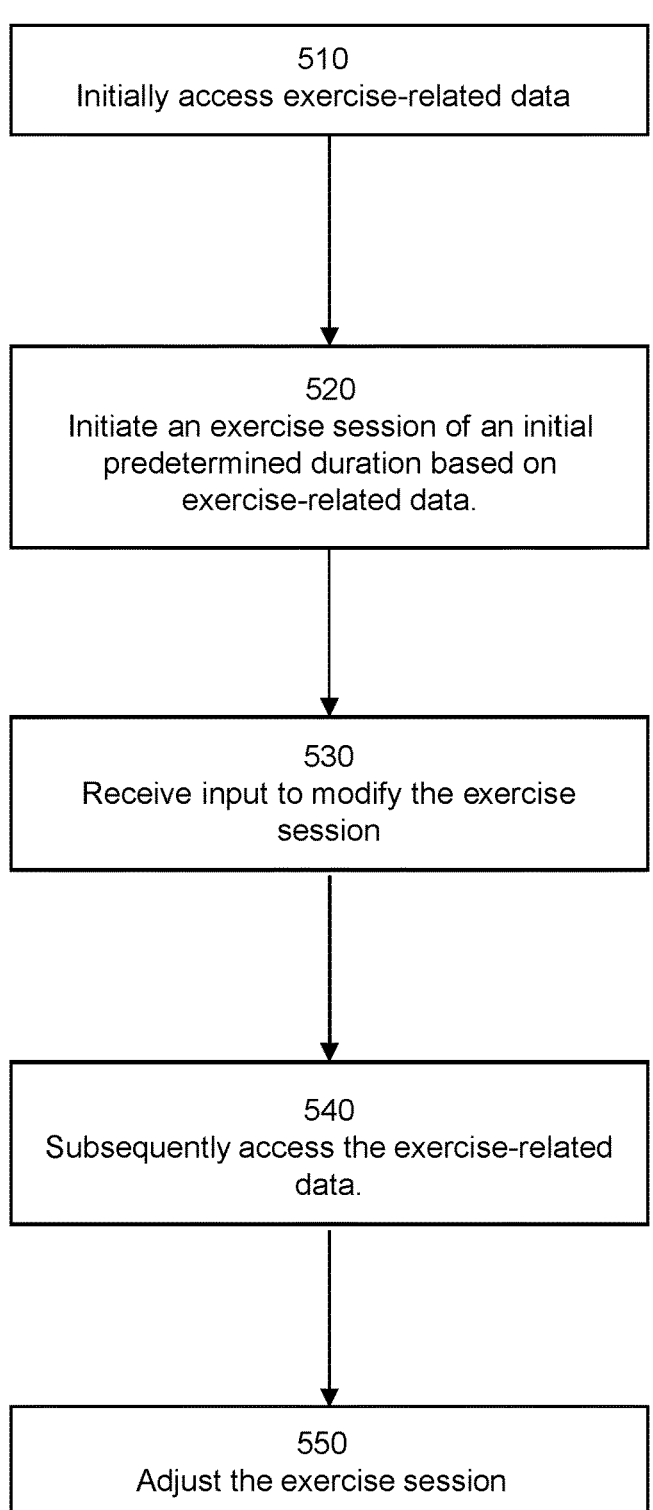
FIG. 5 is a flowchart illustrating a method for adaptive exercise schedule modification.

By way of non-limiting example, FIG. 5 is a block diagram of an exemplary method for adaptively modifying an exercise schedule. Executable code with instructions for causing one or more processors to perform operations set forth in the steps in FIG. 5 may be stored in a non-transitory computer readable medium. Operations may be performed based on instructions executed by, for example, at least one processor such as processor 112 of FIG. 1A. The at least one processor may be configured to perform operations for adaptive exercise schedule modification, as disclosed herein.

In some embodiments, the exercise schedule may include an exercise session, as discussed elsewhere in this disclosure. In some embodiments, the exercise schedule may include information regarding the details of an exercise session and a starting/ending time of the exercise session. In some embodiments, the exercise schedule may include exercise details, for example, a timing, a frequency, a speed, an intensity, a number of repetitions and sets, a duration of time, and/or a mode of one or more exercise routine (e.g., a resistance of a resistance motor of the exercise machine), a configuration of an adjustable piece of exercise equipment, the use of an accessory, a recommended a posture or position of the user, a recommended starting time of day and day of week, and/or an exercise routine. In the context of an exercise machine that has an arm, several aspects may be adjustable including, for example, a height or the angle of the arm, a resistance level of a cable or attachment associated with the arm, or an operation mode associated with a movement or exercise involving the arm.

The exercise schedule may also include sequence of a series of exercises, names of the exercises, exercise goals, and any set up information that may guide a user to perform the exercise or instruct the user to perform or stop performing an exercise. One or more of the foregoing may be adaptable.

Some disclosed embodiments involve initially accessing data. Data, in this context, may include exercise related data including any information that has a bearing on at least one of an exercise, an exercise routine, and individual or a class of individuals associated with an exercise schedule, historical exercise information, or details about a subject individual such as age, height, weight, medical conditions, injuries, restrictions, and/or medical information. Any of such data is "initially accessed" if it precedes some subsequent operation. (I.e., initial accessing does require that the data was not previously accessed.)

In some embodiments, data may be accessed by a processor issuing one or more inquiries to one or more memories or databases in communication with the processor. In addition or alternative to the examples provided above, in some embodiments, the exercise-related data may include an exercise name, an exercise target muscle, an exercise effect, a prohibited condition of the exercise, available/possible resistances, a recommended number of repetitions and sets, a recommended duration of time, a recommended exercise machine adjustment (e.g., a height and/or angle of an arm of the exercise machine, available accessories for the exercise, recommended physiological parameters for user safety, conditions in which the workout should be aborted, and any set up information that may guide a user to perform the exercise or instruct the user to perform or stop performing a task. In some embodiments, the exercise-related data may be preset by an entity such as a manufacturer, owner, operator, trainer, or other entity having control over exercise-related data. In some embodiments, the an initial set of exercise-related data may be preset or determined according to industry standards, scientific research, experience, or a combination thereof. By way of non-limiting example, as shown in the block diagram of FIG. 5, in some embodiments, a processor (such as processor 112) may initially access exercise-related data in step 510. The data may be stored in one or more locations such as in one or more servers or database of a cloud service (such as the cloud service illustrated in FIG. 3), on one or more smart devices such as smartphone 224 of FIG. 3, in a memory of an electronic exercise machine, such as machine 200 shown in FIG. 3, or in any other accessible memory device. The at least one processor may then use exercise-related data to set up an exercise schedule as a starting point.

In some embodiments, the exercise-related data may be associated with an individual's past exercise history. Past exercise history includes any information related to one or more prior exercises performed by the individual. Non-limiting examples of past exercise history include an identification of exercises previously performed by an individual, resistance associated with past exercises performed, historical changes in resistance or exercises, prior injuries or difficulties, In some embodiments, the past exercise history may include past exercise schedule and the degree of execution of the past exercise schedule. In some embodiments, past exercise history may include exercises performed on other machines. The past exercise history may be uploaded from one or more devices, such as smartphone 224, using one or more applications on the device.

In some embodiments, past exercise history may be associated with movements performed on the same exercise machine that is being used for the current exercise session. For example, a processor such as processor 112 may record in memory 114 that a user exercised using a specific exercise schedule on a certain date. If the processor 112 determines that the user completed the exercise schedule with ease (e.g., performed the exercise schedule with high quality, taking short breaks between sets, holding the arm(s) of the exercise machine without much shaking, and/or maintained a low heart rate throughout the scheduled exercise,) the processor 112 may then decide that this exercise schedule might be adjusted to be more challenging (e.g., more resistance, longer duration, more repetitions and sets, higher target heart rate, or using indicators that may indicate the needs of additional efforts.) On the other hand, if the processor 112 determines that the user completed the exercise schedule with much difficulties, (e.g., performed the exercise schedule with low or declining quality, taking long breaks between sets, holding the arm(s) of the exercise machine with much shaking, and/or detected high heart rate during the scheduled exercise,) or even left the exercise schedule without finishing it, the processor 112 may decide that this exercise schedule might be adjusted to be less challenging (e.g., less resistance, shorter duration, fewer repetitions and sets, lower target heart rate, exercise on fewer days every week, or using indicators that may indicate the needs of lower effort.)

In some embodiments, the exercise-related data may include both general exercise data and user specific data. In some embodiments, the exercise machine may recognize a user and use only past exercise history tied to this user. In some embodiments, the exercise machine may recognize a user by asking the user to log in. In some embodiments, the exercise machine may recognize a user by pairing with an identified near field communication (NFC) device, e.g., a smart phone, a smart watch, a wristband, or any NFC enabled device that may be linked to an identify. In some embodiments, the exercise machine may recognize a user by using biometrics of the user, for example, fingerprints, facial recognition, iris scan, voice recognition, body weight, gait analysis, or any other biometrics that can be used to identify a person. Note that such recognition does not need to be done with high confidence (i.e., the level of certainty at the airport security checkpoint.) It only needs to distinguish a limited number of frequent users. For example, the exercise machine may distinguish a husband from a wife by measuring their body weight. In some embodiments, different ways of recognizing a user may be combined for a higher accuracy.

In some embodiments, a user may set up the exercise machine with an exercise goal. The exercise goal may be a general goal, for example, general fitness, weight management, body building, strength, physical therapy. The exercise goal may also be a SMART goal that is "specific, measurable, attainable, relevant, timely." For example, a user may set up the exercise machine by stating that the exercise goal is to "lose ten pounds of weight in a month."

The exercise machine may analyze the exercise goal and the user's physical conditions to determine which exercises to select for an exercise session, and accordingly determine a recommended exercise schedule.

Some embodiments may involve controlling electronic exercise equipment to initiate an exercise session of an initial predetermined duration based on exercise-related data. Electronic exercise equipment refers to fitness equipment that incorporates electronic components and/or features to enhance the workout experience. Examples of electronic exercise equipment includes treadmills (electronics may control one or more of speed, incline, and tracking of workout progress), stationary bikes (, elliptical trainers (with electronically controlled resistance), rowing machines, stair climbers, punching bags with sensor technology, smart dumbbells, balance boards with interactive games, smart jump ropes, interactive fitness mirrors, and smart home gyms, any of the forgoing of which include electronically controlled programmable workouts, pre-programmed workouts, physical adjustments and/or adjustable resistance. As a non-limiting example, electronic exercise equipment may include electronic exercise machine 200 shown in FIGS. 2A-2G and 3.

In some embodiments, an initial predetermined duration may be the predetermined duration in the latest exercise session. In some embodiments, the initial predetermined duration may be a predetermined duration set during manufacturing of the exercise equipment, with a pre-determined value that was decided by the manufacturer, and/or according to scientific research or industry standards. In some embodiments, an exercise session may be associated with one or more different movements, and one or more repetitions of the different movements. A processor may control the exercise equipment to initiate an exercise session by, for example, directly powering and managing the functions of one or more components of the exercise equipment, or by sending a command to another processor of the exercise equipment to operate the exercise equipment components. Control may generally involve the at least one processor managing, running, or commanding the exercise equipment to initiate the exercise session. The predetermined duration may correspond to a length of time, a predetermined number of exercises, a predetermined number of repetitions or sets of exercise, or any other measurable characteristic associated with an exercise session that is associated with duration.

In some embodiments, an exercise session may include a series of varied electronically controlled exercises selected to further an exercise goal. An exercise goal refers to a specific objective or target that an individual sets for themselves in relation to their physical fitness or exercise routine and/or that is set by a computing device. For example, a computing device (e.g., one or more processors) may set a customized exercise goal based on inputs about an individual. In a broadest sense, an exercise goal may be to perform a defined amount of work. An exercise goal may additionally or alternatively include an amount of work for differing exercises or targeting differing regions of the body or muscles. Some exercise goals may additionally or alternatively include burning a number of calories in a workout or over a series of workouts. Additionally or alternatively, an exercise goal may include one or more of weight loss, strength building, endurance improvement, flexibility and mobility and/or athletic performance or any other goal associated with performance qualities. For example, an exercise goal may be associated with a desired strength level, a desired user weight, a target resistance level for one or more movements of an exercise, or any other definable target or desired metric associated with fitness of a user.

An electronically controlled exercise refers to a form of physical activity or workout routine that utilizes electronics to control, monitor, and/or enhance the exercise experience. For example, an electronically controlled exercise includes an exercise where variable resistance is electronically preset. Electronic control may also involve pre-setting other variables such as duration, equipment configuration, electronic coaching, and any other feature that is electronically controllable. Electronic control in some embodiments may involve altering any variable during an exercise routine and/or across a series of sessions.

A series of varied electronically controlled exercises refers to a group of differing exercises that are controlled, as discussed above. The differing exercises may vary in that they are directed to differing parts of the body, differing muscles, or differing manners of exercising the same muscles. Exercises may be additionally or alternatively be varied with respect to a required movement of the exercise equipment, a muscle group targeted by the exercise, a required pose or orientation of the user while interacting with the exercise equipment, or by differentiating other aspects of exercises that result in multiple different exercises.

The series of varied exercises may be a selection from a pool of available exercises on the exercise machine. In some embodiments, the series of varied electronically controlled exercises may be sequenced. In some embodiments, the exercise schedule may refer a particular exercise session, or a particular exercise session within a group of exercise sessions (e.g., spread out over a period of time such as days.) Exercises may be electronically controlled by the exercise equipment by, for example, regulating a resistance level associated with one or more movements of the exercise equipment, by providing feedback or instruction associated with an exercise to a user via an output device.

By way of non-limiting example with reference to step 520 in FIG. 5, a processor (e.g., processor 112) may initiate an exercise session of an initial predetermined duration based on exercise-related data. In some embodiments, one or more processors, such as processor 112, may control one or more motors, such as resistance motor 140 shown in FIGS. 2A and 4, to regulate a resistance level created by resistance motor 140.

Some embodiments involve receiving input to modify the initial predetermined duration to an alternative duration. At some point in an exercise routine or session there may be a set duration for an aspect of the routine or for the entire routine. That predetermined duration may be set by at least one processor in furtherance of achieving the goal, and/or may be set with the involvement of a user (e.g., if the user has a time limitation). After the predetermined duration of the routine is underway, an input may be received to alter the predetermined duration. The alternative duration may be associated with a change in length of time of the exercise session, a change in the exercises or movements or their number in the exercise session, a change in repetitions of one or more exercises in the exercise session, or a change in any other measurable attribute associated with the duration of the exercise session.

The input to alter the duration may be associated with any eventuality. For example, the user may need to shorten the routine in order to meet a time obligation, or the user may simply decide to deviate from the predetermined duration (either shorten or lengthen the duration.) For example, a person in the midst of a workout may need to unexpectedly join a meeting necessitating an abbreviated workout. Or, a meeting may be cancelled, enabling a longer workout.

The input to alter the initial predetermined duration, may be provided at any time, in any form, depending on design constraints of the equipment. For example, the input may be provided on a touchscreen, dial, or other manipulatable control on the equipment or a device paired with the equipment. That user interface may be manipulatable to adjust the predetermined duration. Or, the input may come from a device paired with the equipment (e.g., via a user interface on a paired smartphone). Additionally or alternatively, the equipment or the paired device may be configured to accept voice commands to alter the duration. (E.g., "Hey exercise equipment, shorten the duration of today's session to 45 minutes" or "end today's session by 8:30 am") In yet another example, the input may be automatic. For example, if a user's calendar changes with the addition of an appointment, the exercise equipment or a device paired with the exercise equipment may receive input from the calendar and automatically adjust the routine duration to avoid a calendar conflict. This could occur with reference to preset rules. For example, an adjustable setting may permit a user to select a time buffer between an end of a workout session and a calendar event to give the user sufficient time to cool down or to become presentable.

By way of non-limiting example with reference to step 530 in FIG. 5, a processor (e.g., processor 112) may receive input to modify the exercise session. As discussed, that input may occur via any one of the examples discussed above, or in any other way. For example, an input may be received via manipulation of dial 216 shown in FIGS. 2A, 2F, 2G, and 3. In some embodiments, an input may be received via smartphone 224 or another input device in communication with the at least one processor.

In an example where the received input occurs via a voice command. a microphone may detect voice input from a user. The microphone may be embedded in the exercise equipment, or may be in another device that is in communication with the processor. For example, the microphone may be in a nearby device such as a smartphone or wearable device that is in communication with the processor. In some embodiments, the received input may occur via a control on the exercise equipment. In such embodiments, inputs may be received via one or more input devices on the exercise equipment, such as a touchscreen, touchpad, button press, or other tactile input mechanism. In some embodiments, the received input may occur via a mobile communication device paired with the exercise equipment. In addition to the microphone example provided above, an input interface of a mobile communication device may receive an input associated with adjusting an exercise session, such as using a mobile application associated with the exercise equipment.

In some embodiments, some or all of the input, output, and/or control functions described herein may be provided using an app of a device such as smartphone 224. In such embodiments, the electronic exercise machine may be operated by a user without the user directly interacting with the hardware of the electronic exercise equipment.

In some embodiments, an exercise session adjustment may involve the processor 112 receiving an input to modify the initial predetermined duration to an alternative duration of the exercise session. For example, the processor 112 may receive an input to increase or decrease a duration of the exercise session to an alternative duration that is longer or shorter than the initial predetermined duration. Such input may be received, for example, via one or more input devices on the exercise equipment, or via one or more external devices in communication with processor 112.

In some embodiments, the processor 112 may determine a quality of completion of the exercise session or a part of the exercise session. Processor 112 may receive data associated with movements of the arm(s) of the exercise machine, data associated with the motor, a cable routed through or around the arm of the exercise machine, or a greppable attachment connected to the arm and/or the cable, data associated with accessories connected to or paired with the exercise machine and/or data associated with pictures and/or videos of the user acquired by cameras associated with the exercise machine. Processor 112 may analyze the received data using one or more predetermined metrics associated with the quality of completion. Such movements may include, for example, a movement speed, an acceleration, a start/stop angle, a steadiness, a frequency (as of between repetitions,) an on/off time ratio (as indicator of rest time between sets), a movement distance such as a length of cable pulled or pushed from the machine, a starting and ending position of the cable, or any quantifiable parameter that may indicate the user's easiness to finish an exercise. In some embodiments, the processor may collect such quantifiable parameters using one or more sensors in the exercise equipment or in communication with processor 112, including sensors that continuously or periodically monitor positions of parts of the exercise equipment such as the arm(s) or cable(s) of the equipment. In some embodiments, sensors may detect a position of an individual using the exercise machine, such as a camera detecting a pose of the individual while using the exercise equipment.

Some disclosed embodiments involve altering a resistance on a resistance motor of the electronic exercise equipment. A resistance motor refers to a motor that applies a resistive force. A brushless DC motor (BLDC motor) is one non-limiting example of a motor that can be used to provide resistance. Such a motor may be integrated into the resistance mechanism of the exercise equipment, such as through a flywheel or pulley system. By varying the voltage or current applied to the motor, the resistance level can be adjusted, providing users with different workout intensities. A motor controller may receive input signals via a user interface or smart gym system and regulate the motor's speed and torque output accordingly. This allows users (or a program) to select and adjust the desired resistance level during workouts.

In general, altering the resistance on the resistance motor may change a difficulty or intensity of the exercise. For example, increasing the resistance may increase a simulated amount of weight that must be lifted or force that must be exerted on the exercise equipment in order to complete the exercise movement. The electronic exercise equipment may include one or more resistance motors that generate a resistive force that the individual must overcome to perform the exercise. In some embodiments, the resistance motor may include one or more electromagnets, such as the resistance motors discussed herein.

Some disclosed embodiments involve altering a mode of operation of the electronic exercise equipment. Altering a mode of operation refers to changing or modifying the way the exercise equipment, any part thereof, or any program associated therewith operates. It may involve adjusting one or more settings, parameters, or configurations to alter how the equipment operates. Such changes may impact one or more parameters of the exercise, such as changing an intensity of the exercise. In some embodiments, altering a mode of operation may change the exercise to a different exercise.

Changing the mode of operation may additionally or alternatively include providing electronic instructions to the user to reconfigure the equipment or to use the equipment in a different way. Such instructions may be provided on an equipment display, via a display on a paired device, or thought audibly output instructions.

For example, adjusting a resistive force of the resistance motor changes the amount of force required to perform an exercise. In some embodiments, the mode of operation may be altered by changing a configuration (or instructing a user to change a configuration) of the exercise equipment through, for example a height or angle adjustment (e.g., altering an angle of the arm 212 relative to the exercise equipment). In turn, this alters the manner in which the user performs a movement, or changes a direction that the user faces when performing a movement with the exercise equipment.

Some disclosed embodiments involve outputting instructions for adjusting the electronic exercise equipment. In general, the exercise equipment may provide instructions to a user via one or more output devices in the exercise equipment in a device (e.g., a smartphone) paired with the exercise equipment. The instructions may be provided to users to follow during the exercise session, and in some embodiments, before or after the exercise session, to set up the equipment before a session, and to stow the equipment after use. In some embodiments, outputted instructions may be associated with a change in exercise (e.g., providing instructions adjust parameters of the machine to enable a switch to a different exercise movement. In some embodiments, outputted instructions may be associated with aspects of the exercise other than adjusting the exercise equipment, including a change during a current exercise such as, for example, a change in a number of repetitions, sets, durations, intensity, resistance level, or time of rest between sets of the same exercise movement.

In some disclosed embodiments outputting instructions involve displaying instructions on an electronic display associated with the electronic exercise equipment. Instructions refers to guidance, such as guidance on how to perform an exercise, how to position oneself, or how to configure the exercise equipment. Instructions may be provided in the form of one or more of text, audio, graphics, videos, clips, or images. For example, a display on a piece of exercise equipment or on a paired device may present video instructions, visual images or videos on a display device. A paired device may include a mobile phone or smartphone, tablet, laptop, wearable device, and any other portable or handheld communications device capable of displaying information or providing audible information to a user and communicating with one or more processors of the electronic exercise equipment. The mobile communications device may be paired to the electronic exercise equipment, and may communicate with the exercise equipment via a wired or wireless connection. In some embodiments, the mobile communications device and the exercise equipment may communicate via an intermediary device or system, such as the mobile communications device communicating with the exercise equipment via a local or remote server.

A speaker on either the equipment or a paired device may provide audible queues, spoken instructions output by a speaker, or any other form of communication that can enable a user to understand how to adjust a part of the electronic exercise equipment. An electronic display may be associated with the electronic exercise equipment by being built into the equipment, or by being physically or communicatively attached to the exercise equipment.

By way of non-limiting example, one or more components of an electronic exercise machine, such as machine 200 in FIG. 2A, may provide instructions. For example, with reference to system architecture 100 of FIG. 1A, one or more components of output interface 118 of an electronic exercise machine may display or present instructions to a user. With reference to FIG. 2E, one or more components of a smartphone 224 may provide instructions to a user, such as via a display of the smartphone 224, or other output interface of the smartphone 224.

In some disclosed embodiments, adjusting the exercise session includes outputting instructions for adjusting the electronic exercise equipment. An adjustment of a session may involve changing exercises, and that in turn may involve outputting instructions to effectuate the exercise change. The instructions may be output as described earlier, to guide the user in modifying the equipment (e.g., adjust the equipment for a different exercise. Thus, in the context of a home gym exercise equipment exemplified in the figures, the instructions that may be associated with adjusting an angle or position of an arm of the electronic exercise equipment. In some embodiments, the instructions may be associated with adjusting a height of an arm of the electronic exercise equipment. The instructions may inform a user as to how far to move the arm and in which direction, to reach the required height and/or angle. In some embodiments, the exercise equipment may include one or more sensors for tracking a real-time position of the arm, to provide feedback to the user about how close the arm is to its required angle or height. Such feedback may be provided in the form of updated instructions, or as an indication separate from the outputted instructions.

Some disclosed embodiments involve receiving input to modify the initial predetermined duration to an alternative duration while the exercise session of initial predetermined duration is in progress. For example, in some embodiments, the received input may be an instruction to shorten the initial predetermined duration of the exercise session. In such embodiments, adjusting the exercise session may include shortening non-initiated ones of the varied electronically controlled exercises in a non-linear manner. In some embodiments, the processor 112 may receive input from a user with instructions to change the exercise schedules. Processor 112 may identify exercises in an exercise schedule for the current exercise session, and identify the exercises that have been performed (previously initiated), exercise(s) that are in progress (recently or currently initiated), and exercises that have yet to be performed at all (non-initiated). In such embodiments, processor 112 may determine a shortened length of time associated with the received instruction, and shorten the non-initiated exercises by reducing an amount of allotted time, a number of sets, a number of repetitions, or any other characteristic associated with duration, of the non-initiated exercises. In some embodiments, processor 112 may shorten the non-initiated exercises in a non-linear manner by shortening certain exercises to a greater degree than other exercises. Information associated with the exercise schedule, the exercise session, or the user may identify a hierarchy or priority of exercises, and may perform less shortening of exercises that are deemed to be a higher priority, while shortening low-priority exercises to a greater degree. In some embodiments, user instructions may override such determinations made by the processor 112. In some embodiments, the exercise machine may present a warning in respond to user instructions and require confirmation before shortening exercises.

In some embodiments, the processor 112 may analyze received user instructions to identify patterns and determine user mentalities. For example, processor 112 may determine whether a user has repeatedly provided instructions to reduce an exercise intensity, which may be determined to be associated with a user having less aggressive workout goals, or a preference for lower-intensive exercises. For example, processor 112 may determine that a user has developed a pattern of instructing the exercise equipment to reduce duration and/or intensity more than a threshold number of times over a predetermined time period. In some embodiments, processor 112 may take identified patterns and determined mentality into account for adjusting training schedules and exercise selections.

Some disclosed embodiments involve accessing the exercise-related data. Accessing data refers retrieving or reading information from a storage medium, such as a database, file system, or memory. Any type of the exercise-related data as described earlier, may be accessed depending on the particular need. In some embodiments, for example, the exercise related data may include a set of exercises that are currently planned. Alternatively or additionally, it may include information on how the user previously performed exercises, specific characteristics, abilities, or limitations of the user, or any other information related to user, the exercise goal, or the duration of the current session. By way of example with reference to step 540 in FIG. 5, a processor (e.g., processor 112) may subsequently access the exercise related data, consistent with the description above.

Some disclosed embodiments involve adjusting the exercise session by altering a time of the exercise session and in a manner furthering the exercise goal. Altering a time refers to either shortening or lengthening a duration of the exercise session. In a manner furthering a goal refers to compensating in some way for the time alteration to thereby advance the goal. For example, if altering a time involves shortening a session, then the manner of alteration may involve increasing a resistance level of one or more exercises in the shortened time, to make up for the user adopting a shorter workout. For example, resistance may be increased in one or more exercises so that an amount of work consistent with a goal is achieved by making the user work harder for a shorter period of time.

This may be accomplished by taking into account, the alternative duration, the exercise-related data, the record of the series, and the exercise goal. For example, if a goal is to burn a particular number of calories in a session or to achieve a particular amount of total work or total work in one or more exercises, resistance, speed of repetitions, time between repetitions, and/or any other variable might be changed to minimize the impact on the goal. Thus, the manner of alteration may not ensure that the goal is met, it might help close the gap in achieving the goal. In other embodiments, the manner of furthering the exercise goal may be a manner that maintains the goal. For example, one or more of the aforementioned variables may be altered so that the goal is achieved for the session, despite the altered duration.

Regardless of whether the goal for the session is achieved, the alteration may take into account the exercise-related data, the record of the series, and the exercise goal. For example, the exercise related data may reveal that the user is only capable of a 20% increase in resistance for a particular exercise, when a 30% increase is needed to achieve the goal. In such an instance, the resistance may be increased to 20%, getting the user closer to the goal (i.e., in a manner furthering the goal). In another example, the exercise related data may reveal that the user is capable of a 50% increase in resistance, but given the record of the series, the user only needs a 30% increase in resistance on a particular exercise to meet the goal in the shortened time period. Thus, even though a 50% increase is possible, the system might only apply a 30% increase. This too is a manner furthering the goal. More generally, in order to understand how to adjust a routine to further a goal, the amount of exercise already achieved (i.e., record of the series) is taken into account. If the user is already 90% toward achieving a goal for a session, the adjustment in the routine may be less severe than if the user is only 40% toward attaining the goal. But this too depends on the alternative duration. If the alternative during shortens the routine by only five minutes, the adjustment to the routine will be much less significant that if the routine is cut by 30 minutes.

In some embodiments, the processor 112 may adopt changes that could help the user furthering the user's exercise goal. For example, processor 112 may increase or decrease the time of the exercise session to adjust the exercise session, based on the results of the foregoing steps, to provide an adjusted exercise session tailored to the needs and preferences of the user. The processor 112 may select exercises that are proper for the user's physical conditions, or that would be safe for the user. For example, if a user has a history of very high heart rate after a specific exercise, the heart rate being so high that is higher than the recommended highest heart rate allowed for this exercise, the processor 112 would not select this exercise to further the user's exercise goal. The adjustments of the exercise session may or may not be the same as the exercise session that was initially determined. In some embodiments, processor 112 may select exercises associated with one or more muscle groups that require strength training. For example, accessed exercise-related data may indicate that a user's chest muscles are likely fatigued due to a recent session of chest exercises, and the processor 112 may select exercises associated with different muscle groups such as back or leg muscle groups.

By way of example with reference to step 550 in FIG. 5, a processor (e.g., processor 112) may adjust the exercise session by altering a time of the exercise session and in a manner furthering the exercise goal, consistent with the description above. The processor 112 may compare the current exercise-related data to earlier exercise-related data to evaluate the effects of the changes. In some embodiments, the effects may include a prediction of the user's performance. For example, if the received input was to increase the resistance, past exercise history suggests an already struggling performance, the processor 112 may predict that such change may create a more difficult situation for the user and may not help furthering the user's exercise goals.

Some disclosed embodiments involve determining based on the subsequent access to the exercise related data that the individual requires more emphasis on a particular exercise than on another exercise. For example, one or more processors such as processor 112 may access exercise related data for a user and determine that a particular muscle group of the user is stronger or weaker relative to other muscle groups. Such a determination may be associated with a strength assessment of the user or other information indicative of imbalances in the user's strength or fitness levels. Processor 112 may identify such imbalances and determine one or more exercises expected to strengthen the weaker muscle groups, to resolve the determined imbalances. As another example, processor 112 may receive input from the user or from another individual associated with the user, such as a trainer, that additional emphasis of certain muscle groups or exercises is needed. Processor 112 may identify exercise movements associated with the required emphasis.

Some disclosed embodiments involve allocating more remaining time to the particular exercise than to the another exercise. Remaining time may refer to the duration of the exercise session minus time that has already elapsed. The adjustment may also involve reducing an allocated time amount for other, non-emphasized exercises in the exercise schedule, by reducing a duration of time, repetitions, or sets of the non-emphasized exercises. For example, if exercise data for an individual reflects that the individual's chest muscles are lagging, more chest exercises may be programmed for the time remaining and other muscle groups that are more advanced, may be deemphasized. In some embodiments, adjustment may include shortening at least one rest time between at least two of the series of varied electronically controlled exercises. In such embodiments, processor 112 may shorten of rest time between exercises in addition to or instead of reducing a duration of non-emphasized exercise movements. Such embodiments may therefore maintain or increase an overall intensity level of the non-emphasized exercises, while also emphasizing one or more particular exercise(s) as needed.

Some disclosed embodiments may involve adjusting a subsequent exercise regimen to account for the adjustment to the exercise session. A subsequent exercise regimen refers to a session subsequent to the current session. For example, if certain exercises are cut in a current session, the cut may be made up for by altering the exercises of one or more sessions in the future, as the regime may include one or more sessions spanning a plurality of days (e.g., two or more days, weeks, or months. Thus, the processor 112 may not only adjust a current exercise session, but also adjust subsequent, future exercise sessions. In some embodiments, the exercise schedule, including the selection of exercises, exercise intensity, duration, number of repetitions, number of sets, starting time, number of time the exercise schedule being executed in a set period of time (e.g., a week, a month, a year, or any preset number of days), or any other exercise schedule related factors, may be adjusted based on exercise-related data, the exercise goal, the past exercise schedules, the user's past exercise history, and/or the user's physical conditions.

Systems and methods disclosed herein involve unconventional improvements over conventional approaches. Descriptions of the disclosed embodiments are not exhaustive and are not limited to the precise forms or embodiments disclosed. Modifications and adaptations of the embodiments will be apparent from consideration of the specification and practice of the disclosed embodiments. Additionally, the disclosed embodiments are not limited to the examples discussed herein.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware and software, but systems and methods consistent with the present disclosure may be implemented as hardware alone.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and, accordingly, all suitable modifications and equivalents may be resorted to, falling within the scope of the disclosure.

Computer programs based on the written description and methods of this specification are within the skill of a software developer. The various functions, scripts, programs, or modules may be created using a variety of programming techniques. For example, programs, scripts, functions, program sections or program modules may be designed in or by means of languages, including JAVASCRIPT, C, C++, JAVA, PHP, PYTHON, RUBY, PERL, BASH, or other programming or scripting languages. One or more of such software sections or modules may be integrated into a computer system, non-transitory computer readable media, or existing communications software. The programs, modules, or code may also be implemented or replicated as firmware or circuit logic.

Moreover, while illustrative embodiments have been described herein, the scope may include any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods may be modified in any manner, including by reordering steps or inserting or deleting steps. It is intended, therefore, that the specification and examples be considered as exemplary only, with a true scope and spirit being indicated by the following claims and their full scope of equivalents.

What is claimed is:

1. A non-transitory computer readable medium containing instructions that when executed by at least one processor cause the at least one processor to perform adaptive exercise schedule modification operations, comprising:

initially accessing exercise-related data;

based on the exercise-related data, controlling electronic exercise equipment to initiate an original exercise session of an initial predetermined duration, the original exercise session including a series of varied electronically controlled exercises selected to further an exercise goal;

receiving input to modify the initial predetermined duration to a shorter duration;

subsequently accessing the exercise-related data; and based on the shorter duration, the exercise-related data, a record of the series, and the exercise goal, adjusting the exercise session by shortening a time of the exercise session and adjusting at least one parameter of the series of varied electronically controlled exercises to cause, in the shortened time, a similar exertion as the original exercise session in a manner furthering the exercise goal.

2. The non-transitory computer readable medium of claim 1, wherein the exercise related data is associated with an individual's past exercise history.

3. The non-transitory computer readable medium of claim 1, wherein the operations further comprise receiving input to shorten the initial predetermined duration while the exercise session of initial predetermined duration is in progress.

4. The non-transitory computer readable medium of claim 1, wherein the manner furthering the exercise goal is a manner that maintains the goal.

5. The non-transitory computer readable medium of claim 1, wherein adjusting the exercise session includes shortening non-initiated ones of the varied electronically controlled exercises in a non-linear manner.

6. The non-transitory computer readable medium of claim 1, wherein adjusting the exercise session further includes at least one of altering a resistance on a resistance motor of the electronic exercise equipment or altering a mode of operation of the electronic exercise equipment.

7. The non-transitory computer readable medium of claim 1, wherein adjusting the exercise session includes outputting instructions for adjusting the electronic exercise equipment.

8. The non-transitory computer readable medium of claim 7, wherein the instructions are associated with adjusting an angle of an arm of the electronic exercise equipment.

9. The non-transitory computer readable medium of claim 7, wherein the instructions are associated with adjusting a height of an arm of the electronic exercise equipment.

10. The non-transitory computer readable medium of claim 7, wherein outputting instructions includes displaying instructions on an electronic display associated with the electronic exercise equipment.

11. The non-transitory computer readable medium of claim 7, wherein outputting instructions includes displaying instructions on an electronic display of a mobile communications device paired to the electronic exercise equipment.

12. The non-transitory computer readable medium of claim 7, wherein outputting instructions includes causing audible instructions to be output via a speaker of a mobile communications device.

13. The non-transitory computer readable medium of claim 1, wherein the operations further include determining based on the subsequent access to the exercise related data to emphasize a particular exercise more than another exercise, and wherein adjusting includes allocating more remaining time to the particular exercise than to the another exercise.

14. The non-transitory computer readable medium of claim 1, wherein adjusting includes shortening at least one rest time between at least two of the series of varied electronically controlled exercises.

15. The non-transitory computer readable medium of claim 1, wherein the received input occurs via a voice command.

16. The non-transitory computer readable medium of claim 1, wherein the received input occurs via a control on the exercise equipment.

17. The non-transitory computer readable medium of claim 1, wherein the received input occurs via a mobile communications device paired with the exercise equipment.

18. The non-transitory computer readable medium of claim 1, wherein the operations further comprise adjusting a subsequent exercise regimen to account for the adjustment to the exercise session.

19. The computer readable medium of claim 1, wherein the adjusting the exercise session includes adjusting to avoid a calendar conflict.

20. The computer readable medium of claim 19, further comprising receiving an indication of a change in a calendar, wherein the calendar conflict is associated with the change.

21. A method for performing adaptive exercise schedule modification operations, the method comprising:

initially accessing exercise-related data;

based on the exercise-related data, controlling electronic exercise equipment to initiate an original exercise session of an initial predetermined duration, the original exercise session including a series of varied electronically controlled exercises selected to further an exercise goal;

receiving input to modify the initial predetermined duration to a shorter duration;

subsequently accessing the exercise-related data; and based on the shorter duration, the exercise-related data, a record of the series, and the exercise goal, adjusting the exercise session by shortening a time of the exercise session and adjusting at least one parameter of the series of varied electronically controlled exercises to cause, in the shortened time, a similar exertion as the original exercise session in a manner furthering the exercise goal.

22. A system for performing adaptive exercise schedule modification operations, the system comprising:

at least one processor configured to:

initially access exercise-related data;

based on the exercise-related data, control electronic exercise equipment to initiate an original exercise session of an initial predetermined duration, the original exercise session including a series of varied electronically controlled exercises selected to further an exercise goal;

receive input to modify the initial predetermined duration to a shorter duration;

subsequently access the exercise-related data; and based on the shorter duration, the exercise-related data, a record of the series, and the exercise goal, adjust the exercise session by shortening a time of the exercise session and adjusting at least one parameter of the series of varied electronically controlled exercises to cause, in the shortened time, a similar exertion as the original exercise session in a manner furthering the exercise goal.

\* \* \* \* \*